US009968935B2

(12) United States Patent
Abbott et al.

(10) Patent No.: US 9,968,935 B2

(45) Date of Patent: May 15, 2018

(54) DEVICES FOR CELL ASSAYS

(75) Inventors: Nicholas Abbott, Madison, WI (US); Christopher Murphy, Madison, WI (US); Barbara Israel, Mount Horeb, WI (US); Josh Sotos, Madison, WI (US); Doug Hansmann, Madison, WI (US); Renee Herber, Madison, WI (US); Joseph Burkholder, Middleton, WI (US); Keren Hulkower, Evanston, IL (US); Michael Bonds, Dearfield, WI (US)

(73) Assignee: Platypus Technologies, LLC, Madison ( * ) Notice: Subject to any disclaimer, the term of this patent is extended or adjusted under 35 U.S.C. 154(b) by 816 days.

(21) Appl. No.: 12/195,007

(22) Filed: Aug. 20, 2008

(65) Prior Publication Data

US 2009/0054262 A1 Feb. 26, 2009

Related U.S. Application Data

(60) Provisional application No. 60/965,446, filed on Aug. 20, 2007.

(51) Int. Cl.

| | |
|---|---|
| ***C12M 1/00*** | (2006.01) |
| ***G01N 33/53*** | (2006.01) |
| ***C12M 3/00*** | (2006.01) |
| ***B01L 3/00*** | (2006.01) |

(52) U.S. Cl.

CPC ..... *B01L 3/5085* (2013.01); *B01L 2200/0668* (2013.01); *B01L 2300/0829* (2013.01); *B01L 2300/0851* (2013.01)

(58) Field of Classification Search

CPC . B01L 3/5085; B01L 2300/0829; C12M 1/00; C12M 3/00; G01N 33/53

USPC ................................................ 435/288.1, 7.1

See application file for complete search history.

(56) References Cited

U.S. PATENT DOCUMENTS

| | | | |
|---|---|---|---|
| 2,639,815 | A | 5/1953 | Paluck |
| 3,645,693 | A | 2/1972 | Poziomek et al. |
| 3,883,398 | A | 5/1975 | Ono |
| 3,910,763 | A | 10/1975 | Poziomek et al. |
| 4,068,925 | A | 1/1978 | Tani et al. |
| 4,096,086 | A | 6/1978 | Kanbe et al. |
| 4,285,697 | A | 8/1981 | Neary et al. |
| 4,297,879 | A | 11/1981 | Howells |
| 4,551,264 | A | 11/1985 | Eidenschink et al. |
| 4,597,942 | A | 7/1986 | Meathrel et al. |
| 4,612,873 | A | 9/1986 | Eberle |
| 4,795,253 | A | 1/1989 | Sandridge et al. |
| 5,055,408 | A | 10/1991 | Higo et al. |
| 5,059,394 | A | 10/1991 | Phillips et al. |
| 5,063,024 | A | 11/1991 | Partanen et al. |
| 5,073,294 | A | 12/1991 | Shannon et al. |
| 5,132,226 | A | 7/1992 | Dreher et al. |
| 5,141,718 | A | 8/1992 | Clark et al. |
| 5,298,394 | A | 3/1994 | Arima et al. |
| 5,302,515 | A | 4/1994 | Goodwin |
| 5,355,215 | A | 10/1994 | Schroeder et al. |
| 5,370,841 | A | 12/1994 | McDonnel et al. |
| 5,474,796 | A | 12/1995 | Brennan |
| 5,484,565 | A | 1/1996 | Larsen et al. |
| 5,599,919 | A | 2/1997 | Yen et al. |
| 5,601,980 | A | 2/1997 | Gordon |
| 5,700,637 | A | 12/1997 | Southern |
| 5,801,055 | A | 9/1998 | Henderson |
| 5,858,650 | A | 1/1999 | Sapolsky et al. |
| 5,908,786 | A | 6/1999 | Moreno et al. |
| 5,925,525 | A | 7/1999 | Fodor et al. |
| 5,985,551 | A | 11/1999 | Brennan |
| 6,001,311 | A | 12/1999 | Brennan |
| 6,017,696 | A | 1/2000 | Heller |
| 6,040,193 | A | 3/2000 | Winkler et al. |
| 6,045,996 | A | 4/2000 | Cronin et al. |
| 6,051,380 | A | 4/2000 | Sosnowski et al. |
| 6,068,818 | A | 5/2000 | Ackley et al. |
| 6,171,780 | B1 | 1/2001 | Pham et al. |
| 6,171,802 | B1 | 1/2001 | Woolverton et al. |
| 6,201,588 | B1 | 3/2001 | Walton et al. |
| 6,242,266 | B1 | 6/2001 | Schleifer et al. |
| 6,277,489 | B1 | 8/2001 | Abbott et al. |
| 6,277,490 | B1 | 8/2001 | Ruf |

(Continued)

FOREIGN PATENT DOCUMENTS

| | | | |
|---|---|---|---|
| EP | 1549953 | A2 | 5/2004 |
| WO | 91/05036 | A2 | 4/1991 |

(Continued)

OTHER PUBLICATIONS

Detrait et al. (Orientation of cell adhesion and growth on patterned heterogeneous polystyrene surface, 1998, Journal of Neuroscience Methods, vol. 84, pp. 193-204).*

Kam et al. A Novel Circular Invasion Assay Mimics In Vivo Invasive Behavior of Cancer Cell Lines and Distinguishes Single-Cell Motility In Vitro; BMC Cancer, vol. 8, No. 198, pp. 1-12. (Year: 2008).*

Van Horssen et al. Differential Effects of Matrix and Growth Factors on Endothelial and Fibroblast Motility: Application of a Modified Cell Migration Assay; Journal of Cellular Biochemistry, vol. 99, pp. 1536-1552. Year: 2006).*

(Continued)

*Primary Examiner* — Scott Long

*Assistant Examiner* — Paul C Martin

(74) *Attorney, Agent, or Firm* — Casimir Jones S.C.; J. Mitchell Jones

(57) ABSTRACT

The present invention relates to the field of molecular diagnostics. In particular, the present invention provided improved substrates and methods of using liquid crystals and other biophotonically based assays for quantitating the amount of an analyte in a sample. The present invention also provides materials and methods for detecting non-specific binding of an analyte to a substrate by using a liquid crystal or other biophotonically based assay formats.

8 Claims, 13 Drawing Sheets

(56) References Cited

U.S. PATENT DOCUMENTS

| | | | |
|---|---|---|---|
| 6,284,197 | B1 | 9/2001 | Abbott et al. |
| 6,288,392 | B1 | 9/2001 | Abbott et al. |
| 6,306,659 | B1 | 10/2001 | Parce et al. |
| 6,410,687 | B1 | 6/2002 | Vale et al. |
| 6,444,254 | B1 | 9/2002 | Chilkoti et al. |
| 6,468,657 | B1 | 10/2002 | Hou et al. |
| 6,527,115 | B2 | 3/2003 | Rabiner et al. |
| 6,586,257 | B1 | 7/2003 | Vuong |
| 6,596,545 | B1 | 7/2003 | Wagner et al. |
| 6,632,655 | B1 | 10/2003 | Mehta et al. |
| 6,692,699 | B2 | 2/2004 | Abbott et al. |
| 6,780,492 | B2 | 8/2004 | Abbott |
| 6,797,463 | B2 | 9/2004 | Abbott et al. |
| 6,811,752 | B2 | 11/2004 | Barbera-Guillem |
| 6,824,837 | B2 | 11/2004 | Abbott |
| 6,844,184 | B2 | 1/2005 | Kim et al. |
| 6,849,321 | B2 | 2/2005 | Abbott et al. |
| 6,852,285 | B2 | 2/2005 | Abbott et al. |
| 6,858,423 | B1 | 2/2005 | Abbott et al. |
| 6,884,357 | B2 | 4/2005 | Siddiqi |
| 6,982,171 | B2 | 1/2006 | Kim |
| 7,018,838 | B2 | 3/2006 | Murphy et al. |
| 7,125,592 | B2 | 10/2006 | Abbott |
| 7,135,143 | B2 | 11/2006 | Abbott |
| 7,303,694 | B2 | 12/2007 | Murphy et al. |
| 7,332,328 | B2 | 2/2008 | Webb |
| 7,371,563 | B2 | 5/2008 | Duffy et al. |
| 7,374,906 | B2 | 5/2008 | Kirk |
| 7,390,463 | B2 | 6/2008 | He et al. |
| 7,452,726 | B2 | 11/2008 | Chou et al. |
| 7,459,124 | B2 | 12/2008 | Abbott |
| 7,470,533 | B2 | 12/2008 | Xu |
| 7,531,366 | B2 | 5/2009 | Abbott |
| 7,662,572 | B2 | 2/2010 | Abbott et al. |
| 7,662,751 | B2 | 2/2010 | Abbott |
| 7,666,661 | B2 | 2/2010 | Abbott |
| 7,732,152 | B2 | 6/2010 | Abbott |
| 7,795,007 | B2 | 9/2010 | Abbott |
| 7,807,348 | B2 | 10/2010 | Abbott |
| 7,842,499 | B2 | 11/2010 | Abbott |
| 7,910,382 | B2 | 3/2011 | Abbott |
| 7,951,577 | B2 | 5/2011 | Murphy |
| 8,268,614 | B2 | 9/2012 | Murphy et al. |
| 2002/0004216 | A1 | 1/2002 | Abbott et al. |
| 2002/0028451 | A1 | 3/2002 | Abbott et al. |
| 2002/0052002 | A1 | 5/2002 | Niehaus et al. |
| 2002/0055093 | A1 | 5/2002 | Abbott et al. |
| 2002/0117412 | A1 | 8/2002 | Rabiner et al. |
| 2002/0123134 | A1 | 9/2002 | Huang et al. |
| 2002/0142453 | A1 | 10/2002 | Abbott et al. |
| 2002/0164604 | A1 | 11/2002 | Abbott et al. |
| 2002/0172621 | A1 | 11/2002 | Barbera-Guillem |
| 2002/0173033 | A1 | 11/2002 | Hammerick et al. |
| 2002/0179439 | A1 | 12/2002 | Weng |
| 2003/0004986 | A1 | 1/2003 | Lin et al. |
| 2003/0032046 | A1 | 2/2003 | Duffy et al. |
| 2003/0040087 | A1 | 2/2003 | Kim et al. |
| 2003/0071949 | A1 | 4/2003 | Abbott |
| 2003/0099993 | A1 | 5/2003 | Abbott et al. |
| 2003/0113812 | A1* | 6/2003 | Hemperly ...................... 435/7.2 |
| 2003/0124029 | A1 | 7/2003 | Webb et al. |
| 2003/0127396 | A1 | 7/2003 | Siddiqi |
| 2003/0180966 | A1 | 9/2003 | Abbott |
| 2003/0194753 | A1 | 10/2003 | Abbott |
| 2003/0215449 | A1 | 11/2003 | Mezes et al. |
| 2004/0002131 | A1 | 1/2004 | Kim et al. |
| 2004/0009162 | A1 | 1/2004 | Pfaff et al. |
| 2004/0009583 | A1 | 1/2004 | Benn et al. |
| 2004/0038408 | A1 | 2/2004 | Abbott et al. |
| 2004/0062882 | A1 | 4/2004 | Liebmann-Vinson et al. |
| 2004/0091620 | A1 | 5/2004 | Abbott |
| 2004/0142411 | A1 | 7/2004 | Kirk et al. |
| 2004/0161800 | A1 | 8/2004 | Abbott et al. |
| 2004/0224380 | A1 | 11/2004 | Chou et al. |
| 2005/0009113 | A1 | 1/2005 | Goldbard et al. |
| 2005/0064395 | A1 | 3/2005 | Israel et al. |
| 2005/0079486 | A1 | 4/2005 | Abbott |
| 2005/0079487 | A1 | 4/2005 | Murphy et al. |
| 2005/0106562 | A1 | 5/2005 | Abbott |
| 2005/0112544 | A1 | 5/2005 | Xu et al. |
| 2005/0158880 | A1* | 7/2005 | Ostuni et al. ..................... 438/1 |
| 2005/0221271 | A1 | 10/2005 | Abbott |
| 2005/0260703 | A1 | 11/2005 | Abbott |
| 2006/0003389 | A1 | 1/2006 | Abbott |
| 2006/0141446 | A1 | 6/2006 | Abbott |
| 2006/0252031 | A1 | 11/2006 | Abbot |
| 2007/0004046 | A1 | 1/2007 | Abbott |
| 2007/0042505 | A1 | 2/2007 | Abbott |
| 2007/0099249 | A1 | 5/2007 | Abbott |
| 2007/0104612 | A1 | 5/2007 | Abbott |
| 2007/0110614 | A1 | 5/2007 | Abbott |
| 2007/0231832 | A1 | 10/2007 | Abbott |
| 2007/0269848 | A1 | 11/2007 | Abbott |
| 2008/0050799 | A1 | 2/2008 | Abbott |
| 2008/0160539 | A1 | 7/2008 | Abbott |
| 2008/0187949 | A1 | 8/2008 | Goldbard et al. |
| 2009/0054262 | A1 | 2/2009 | Abbott et al. |

FOREIGN PATENT DOCUMENTS

| | | | | |
|---|---|---|---|---|
| WO | WO 91/18653 | A2 | | 12/1991 |
| WO | WO 99/63329 | | | 12/1999 |
| WO | WO 00/50570 | A2 | | 8/2000 |
| WO | 00/60356 | A1 | | 10/2000 |
| WO | 00/73799 | | | 12/2000 |
| WO | WO 01/61325 | A2 | | 8/2001 |
| WO | WO 01/61325 | A3 | | 8/2001 |
| WO | WO 01/61357 | A2 | | 8/2001 |
| WO | WO 01/61357 | A3 | | 8/2001 |
| WO | WO 02/071929 | A2 | | 9/2002 |
| WO | WO 02/075294 | | | 9/2002 |
| WO | WO 03/019191 | | | 3/2003 |
| WO | WO 03/021339 | A2 | | 3/2003 |
| WO | WO 03/021339 | A3 | | 3/2003 |
| WO | 03/029418 | A2 | | 4/2003 |
| WO | WO 03/029481 | | | 4/2003 |
| WO | WO 03/081230 | | | 10/2003 |
| WO | WO 03/086197 | | | 10/2003 |
| WO | WO 04/041061 | | | 5/2004 |
| WO | WO 04/044583 | | | 5/2004 |
| WO | WO 05/010160 | | | 2/2005 |
| WO | 05/047863 | | | 5/2005 |
| WO | WO 05/047863 | | * | 5/2005 |
| WO | 08/069752 | | | 6/2008 |

OTHER PUBLICATIONS

Gupta et al, "Optical Amplification of Ligand-Receptor Binding Using Liquid Crystals," Science vol. 279, Mar. 27, 1998 pp. 2077-2080.

Green et al., "Mechanism of the Transformation of a Stiff Polymer Lyotropic Nematic Liquid Crystal to the Cholesteric State by Dopant-Mediated ChiralInformation Transfer", J. Am. Chem. Soc., 1998. 120,9810-9817.

Seung Ryeol Kim et al.. Anal. Chem "A Possible Substrate for Biomolecular Assays Based on Lquid Crystals, Analytical 2 Chemistry,"(2000) 72(19);4646-4653.

Lauer L. et al, "Spot Complaint Neuronal Networks by Structure Optimized Micro-Contact Printing" Biomaterials, Elsevier Science, 2001, vol. 22, pp. 1925-1932.

Kikuchi H E et al, "Culture of Bone-Marrow-Derived Cells in Microfabricated Pit Arrays" Proc SPIE Int Soc Opt Eng; 2001, vol. 4265, pp. 40-49.

Iwuoha E I et al: Reactivities of Organic Phase Biosensors 3: Electrochemical Study of Cytochrome P450 CAM Immobilized in a Methyltriethoysilance Sol-Gel Electroanalysis, VHC Publishers Inc. ( 2000) vol. 12, p. 980.

Skaife, Justin G et al.. "Quantitative Interpretation of the Optical Textures of Liquid Crystals Caused by Specific Binding of Immunoglobulins to Surface-Bound Antugens," Langmuir (2000) 16(7):3529-3536.

(56) References Cited

OTHER PUBLICATIONS

Skaife, Justin G et al, "Quantitative Characterization of Obliquely Deposited Subtrates of Gold by Atomic Force Microscopy: Influence of Subtrate Topography on Anchoring of Liquid Crystals" Chemistry of Materials, V 11(3) 1999, pp. 612-623.
Vinay K. Gupta et al. "Using Droplets of Nematic Liquid Crystal to Probe the Microscopic and Mesoscopic Structure of Organic Surfaces," Langmuir 15:21 (1999) 7213-7223.
R.R. Shah et al.. "Principles for Measurement of Chemical Exposure Based on Recognition-Driven Anchoring Transitions in Liquid Crystals," Science (2001) 393(5533):1296-99.
Kleinfeld D. et al., "Controlled Outgrowth of Dissociated Neurons on Patterned Substrates," J. Neurosci. 1988 8:4098 120.
Kumar et al.. "Patterned Self-Assembled Monolayers and Meso-Scale Phenomena," Langmuir (1994) 10:1498 511.
Xia Y, "Use of Controlled Reactive Spreading of Liquid Alkanethiol OD the Surface of Gold to Modify the Size of Features Produced by Mierocontact Printing," Whitesides, G., J. Am. Chem. Soc. (1995) 117:327475.
Hickman et al.,"Rational pattern design for in vitro cellular networks using surface photochemistry," J. Vac. Sci. Technol. (1994) 12:607 16.
Jerome, Blandine, "Surface effects and anchoring in liquid crystals," Rep. Prog. Phys. (1991) 54:391 451.
Gupta et al. Design of Surfaces for Patterned Alignment of liquid Crystals on Planar and Curved Substrates, Science (1997) 276:1533-1536.
Drawhorn et al, "Anchoring of Nematic Liquid Crystals on Self-Assembled Monolayers Formed from Alkanethiols on Semitransparent Films of Gold," J. Phys. Chem. (1995) 45:16511.
Ladam, Guy et al, "Protein Adsorption onto Auto-Assembled Polyelectrolyte Films," Langmuir (2001) 17(3):878-882.
Wagner et aL "Covalent Immobilization of Native Biomolecules onto Au(111} via N-Hydroxysuccinimide Ester Functionalized Self-Assembled Monolayers for Scanning Probe Microscopy," Biophys. J. (1996) 70:2052 2066.
Tarlov et al.,"UV Photopatterning of Alkanethiolate Monolayers," J. Am. Chem. Soc (1993) 115: 5305.
Kumar et aL, "Patterned Self-Assembled Monolayers and Meso-Scale Phenomena," Acc. Chem. Res. (1995) 28: 219.
Resler D. P et al, "High-efficiency liquid-crystal optical phased-array beam steering," Opt. Lett. (1996) 21, 689.
Stern, Margaret B, "Binary Optics: A VLSI-based microoptics technology," Microelectron. Eng. (1996) 32. 369.
Goto et aL, "Design of an Aberration-Free Spherical Micro Lens with a Diffractive Relief Grating Film on a Refractive Spherical Glass Substrate," Jpn. J. AppL Phys. (1992) 31,1586.
Magiera et aL,"Hybrid Imaging Element—Possibilities of Aberration Correction," Soc. Photo Opt. Instrum. Eng., (1996) 2774, 204.
Bernard, et al. Affinity capture of proteins from solution and their dissociation by contact printing. Nature Biotechnology. 2001; 19(9):866-869.
Renault et al. "Fabricating Microarrays of Functional Proteins Using Affinity Contact Printing." Angew. Chem. Int. Ed. 2002; 41 (13):2320-2323.
Fast, Cheap, Portable: A New Pathogen Detection Tool. Biomedical Instrumentation & Technology.2002; 36(1): 15.
Woolverton, et al. A liquid crystal biosensor for virus detection. Abstracts of the General Meeting of the American Society for Microbiology. 2002;102:110-111. (Abstract Only) (1 PG.).
Espinopza LA, Schumann KR, Luk YY, Israel BA, Abbott NL; Orientational Behavior of Thermotropic Liquid Crystals on Surfaces Presenting Electrostatically Bound Vesicular Stomatitis Virus. Langmuir (2004) Mar. 16; 20(6):2375-85.
Tingey et al. "Imaging of Affinity Microcontact Printed Proteins by Using Liquid Crystals:" Langmuir.2004; 20:6816-6826.
Kim, et al. "Orientation of Liquid Crystals on Mechanically Rubbed Films of Bovine Serum Albumin: A possible Substrate for Biomolecular Assays Based on Liquid Crystals", Anal. Chem. vol. 72, No. 19, Oct. 1, 2000, pp. 4646-4653.
Kleinfeld et al, "Controlled Outgrowth of Dissociated Neurons on Patterned Substrates," Journal of Neuroscience, (1988) 8 (11): 4098-4120.
Extended European Search Report, EP Patent Application No. 08827948.4, dated Apr. 15, 2015.
Dulcey C.S., "Deep UV photochemistry of chemisorbed monolayers: patterned coplanar molecular assemblies." Science,1991, 252(5005):551-4.
EP Office Action, EP Patent Application No. 08827948.4, dated Mar. 17, 2016.
Charych, Deborah H., et al., "Direct Colorimetric Detection of a Receptor-Ligand Interaction by a Polymerized Bilayer Assembly," Science; 1993; 261(5121): 585-588.

* cited by examiner

A B

DEVICES FOR CELL ASSAYS

The Application claims the benefit of U.S. Prov. Appl. 60/965,446, filed Aug. 20, 2007, which is incorporated by reference in its entirety.

This application was made with the support of Nat'l Institute of General Medical Sciences (NIGMS) grant 2R44GM069026-03. The government may have certain rights in this invention.

FIELD OF THE INVENTION

The present invention relates to the fields of molecular biology, cellular biology, developmental biology, stem cell differentiation, immunology, oncology, general laboratory sciences and microbiology, and in particular to methods and compositions based on liquid crystal assays and other biophotonic based assays for detecting and quantifying the number of cells present on a test surface or within a test substrate and the proliferation, death or movement of cells under controlled conditions and in response to chemotactic and other cytoactive (including compounds that are chemokinetic but not chemotactic and agents that inhibit cell migration) agents.

BACKGROUND OF THE INVENTION

Cell migration is intrinsic to cancer, wound healing, including both the promotion and inhibition of select cell populations to arrive at optimal outcomes (e.g., keloid formation where an exaggerated wound healing response results in excessive tissue formation), vasculogenic pathologies (e.g. diabetic retinopathy, age related macular degeneration, retinopathy of prematurity), inflammatory (e.g. migration of macrophages, neutrophils, eosinophils, basophils, lymphocytes and related cells) and normal and abnormal developmental processes.

Every year cancer claims the lives of hundreds of thousands of people worldwide. The populations of many of the heavily industrialized countries are particularly susceptible to cancer induced morbidity and mortality. In fact, cancer is the second leading cause of death in industrialized nations. For example, prostate cancer is the second most common malignancy in men. It is estimated that in 2002 in the United States nearly 180,000 men will be diagnosed with prostate cancer. Breast cancer is the most common female malignancy in most industrialized countries, and in the United States it is estimated that breast cancer will affect about 10% of women during their lives. Approximately 30 to 40% of women with operable breast cancer eventually develop metastases distant from the primary tumor.

Metastasis, the formation of secondary tumors in organs and tissues remote from the site of the primary tumor, is the main cause of treatment failure and death for cancer patients. Indeed, the distinguishing feature of malignant cells is their capacity to invade surrounding normal tissues and metastasize through the blood and lymphatic systems to distant organs. Cancer metastasis is a complex process by which certain cancer cells acquire substantial genetic mutations and perturbed signal cascades that allow them to leave the primary tumor mass and establish secondary tumors at distant sites. Metastatic cancer cells break adhesions with neighboring cells, dissolve the extracellular matrix, migrate and invade surrounding tissue, travel via the circulatory system, invade, survive and proliferate in new sites. Unfortunately, the molecular mechanisms that promote and restrain the metastatic spread of cancer cells have yet to be clearly identified.

Medical researchers have made considerable efforts to understand whether chemotactic agents are involved in metastasis and why particular cancers preferentially metastasize to certain sites. Breast cancer, for example, favors metastasizing to regional lymph nodes, bone marrow, and lung and liver tissues. Prostate cancer favors metastasizing to bone marrow. Several theories have been advanced to explain the preferential metastasis of certain cancers.

It has recently been shown that one important property of highly metastatic cells is their ability to respond to chemotactic agents such as paracrine and autocrine motility factors. For example, recent work done by Muller et al. provides evidence for chemotactic homing of breast cancer to metastatic sites. (Muller et al. "*Involvement of chemokine receptors in breast cancer metastasis*," Nature, 410:50-56 [2001]); See also, M. More, "*The role of chemoattraction in cancer metastases*," Bioessays, 23:674-676 [2001]). Muller et al. findings indicate that CXCR4 and CCR7 chemokine receptors are found on breast cancer cells and that ligands for these receptors are highly expressed at sites associated with preferential breast cancer metastases.

Previously described cell migration assays suffer from several problems. In particular, the assays are not standardized, lack sensitivity and reproducibility, and are not adaptable for conducting large numbers of assays in parallel.

What are needed are assay devices and systems for detecting and quantifying cell number and identifying their spatial location, wherein the systems are standardized and amenable to performing assays in parallel.

SUMMARY OF THE INVENTION

The present invention relates to the fields of molecular biology, cellular biology, immunology, oncology, developmental biology, stem cell differentiation, general laboratory sciences and microbiology, and in particular to methods and compositions based on liquid crystal assays and other biophotonically based assays for detecting and quantifying the number of cells present on a substrate (allows for the quantitation of cell adhesion and cell proliferation) as well as direct quantification of proliferation, cell death, differentiation, or cell migration on a surface or through an extracellular matrix (cell invasion) under controlled conditions and in response to the presence of chemotactic, growth, differentiation enhancing and other cytoactive (accounts for chemokinetic agents and agents that inhibit cell migration) agents.

In some embodiments, the present invention provides systems, device and kits comprising: a substrate comprising one or more cell assay zones and one or more cell exclusion zones and one or more spatially distinct cell seeding zones; and optionally a mask configured to interface with the substrate, the mask having one or more apertures and aligned with the cell assay zones. In some embodiments, each of the cell assay zones has one or more cell assay zones and one or more spatially distinct seeding zones. In some embodiments, the substrate is coated with a coating material comprising protein or polysaccharide. In some embodiments, the area of the mask aperture is larger than area of the cell exclusion zone and smaller than the cell seeding zone so that a portion of the cell seeding zone is exposed by the aperture to form an analytic zone. In further embodiments, the cell exclusion zones are circular and have a defined diameter and wherein the diameter of the mask aperture is from about 20% smaller to about 20% larger than the diameter of the cell exclusion zone. In other embodiments, the cell exclusion zones are circular and have a defined diameter and wherein the diameter of the mask aperture is from about 0.1 mm to about 20 mm larger than the diameter of the cell exclusion zone. In some embodiments, mask comprises a fluorescent tag adjacent to the mask aperture. In some embodiments, the mask has therein an additional priming aperture for each aperture in the mask, wherein the priming aperture exposes the cell seeding region. In some embodiments, the substrate is a multiwell plate. In some embodiments, the cell assay or analytic zone is on the bottom of a well in the multiwell plate. In some embodiments, the cell exclusion zone has a shape selected from the group consisting of square, rectangular crescent, triangular, pentagonal, hexagonal, and stellate. In some embodiments, the substrate is a 24, 96, 384 or 1536 multiwell plate.

In some embodiments, the present invention provides methods of assaying cells comprising: providing a substrate comprising one or more cell assay zones each comprising a cell exclusion zone adjacent to a cell seeding zone and a mask configured to interface with the substrate, the mask having one or more apertures therein; seeding cells in the cell seeding zones; incubating the substrate to allow cell attachment; incubating the substrate to allow cell movement into the cell assay zones; aligning the mask with the substrate; and reporting the presence of cells within the analytic zone. In some embodiments, the substrate or the seeded cells are coated with a coating material comprising protein or polysaccharide. In some embodiments, the cells are labeled with a fluorophore. In some embodiments, the step of determining the number of cells within the analytic zone comprises irradiating the analytic zone with light. In some embodiments, the light is absorbed by an added reagent or excites a fluorophore. In some embodiments, the absorbed light or excited fluorophore is read by microscopy, a plate reader reading optical density and/or fluorescence, a microarray reader, a CCD, a photodiode, a spectrometer, a scanner, a digital imaging device or instrument, the eye, a flat bed scanner or a multi-channel infrared scanner. In some embodiments, the reporting is by a plate-reader. In some embodiments, the step of determining the number of cells within the analytic zone comprises irradiating the analytic zone and adhered fluorescent tag with light. In some embodiments, the step of determining the number of cells within the analytic zone comprises irradiating the analytic zone and adjacent priming aperture with light.

In some embodiments, the present invention provides methods of assaying cells comprising: providing a substrate comprising one or more cell assay zones each comprising a cell exclusion zone adjacent to a cell seeding zone and a mask configured to interface with the substrate, the mask having one or more apertures therein, wherein the area of the apertures is larger than area of the cell exclusion zone and smaller than the cell seeding zone so that a portion of the cell seeding zone is exposed by the aperture when the mask and the substrate are aligned; seeding cells in the cell seeding zones; incubating the substrate to allow cell movement into the cell assay zones; aligning the mask with the substrate so that the array of cells assay zones is aligned with the array of apertures; and determining the number of cells within the analytic zone.

In some embodiments, the present invention provides systems, device and kits comprising: a substrate comprising an array of cell assay zones each comprising a cell exclusion zone adjacent to a cell seeding zone, wherein the cell exclusion zone comprises a polymer to block adherence of cells to the substrate surface of the cell exclusion zone. In some embodiments, the polymer is a biopolymer. In some embodiments, the biopolymer is selected from the group consisting of polysaccharide carbohydrates and nucleic acid. In some embodiments, the polysaccharide carbohydrates is selected from the group consisting of alginate, hyaluronic acid, starch glycogen, cellulose, chitin, xanthan gum, dextran, gellan gum, glucomannan, hydroxypropyl cellulose, hydroxypropylmethyl cellulose, carboxymethyl cellulose, carageenan, inulin, agarose and pullulan. In some embodiments the nucleic acid is selected from the group consisting of ribonucleic acid, single stranded deoxyribonucleic acid (ssDNA), and double-stranded deoxyribonucleic acid (dsDNA). In some embodiments, the dsDNA contains a specific nucleotide sequence that is recognized and subsequently cleaved by a restriction endonuclease. In some embodiments, the polymer is selected from the group consisting of polymers formed from or comprising sodium poly(styrene sulfonate), n-butyl hemiester of [poly(maleic anhydride-alt-2-methoxyethyl vinyl ether), N-isopropylacrylamide copolymers, poly(lactic acid) and poly[(lactic acid)-co-(glycolic acid)], hyaluronic acid and pluronics, N-isopropylacrylamide copolymers; cellulose acetate butyrate-pH/thermosensitive polymers, ethyleneglycol-terminated polymers, perfluorocarbon terminated polymers, carbopol, polyvinylpyrrolidone, polyvinyl alcohol and polyethylene glycol.

In some embodiments, the polymer is thermosensitive. In some embodiments the thermosensitive polymer is selected from Poly(N-isopropylacrylamide) (PNiPAAm), poly(N,N-diethylacrylamide) (PDEAAm), poly(N-isopropylacrylamide)-poly(ethylene glycol)-thiol (PNIPAAm-PEG-thiol), pluronic gels [e.g., poly(ethylene oxide) and poly(propylene oxide), poly(ethylene oxide) and poly(propylene oxide)], copolymers [e.g., N-isopropylacrylamide and diethyleneglycol methacrylate (poly(NiPAAm-co-DEGMA)] and elastin-like polypeptides. In some embodiments the thermosensitive polymer is dispersed upon heating. In some embodiments, illumination of the polymer, deposited on the well bottom, through the mask leads to removal of the polymer based on upon local heating. In some embodiments, the thermopolymer is dispersed upon cooling. In some embodiments, the polymer allows cell attachment at 37 degrees C. but releases the attached cells upon cooling.

In some embodiments, the polymer is degradable. In some embodiments, the degradable polymer is hydrolysable upon exposure to an aqueous solution. In some embodiments, the polymer is heat labile. In some embodiments, the polymer is thixotropic. In some embodiments, the polymer comprises magnetic particles. In some embodiments, the devices comprise a non-degradable layer adhered to the degradable polymer. In some embodiments, the polymer can be modified to allow cell adherence. In some embodiments, the polymer is selected from the group consisting of ethylene glycol and perfluorocarbon terminated polymers. In some embodiments, the polymer can be functionalized. In some embodiments, the polymer is polyethylene glycol. In some embodiments, polymer is functionalized with biotin. In some embodiments, the devices and systems further comprise a mask configured to interface with the substrate. In some embodiments, the mask has an array of apertures therein so that when the mask is placed adjacent to the substrate the array of cells assay zones is aligned with the array of apertures, wherein the area of the aperture is larger than area of the cell exclusion zone and smaller than the cell seeding zone so that a portion of the cell seeding zone is exposed by the aperture. In some embodiments, the polymer comprises a blend of two or more polymers (glucomannan and gelatin). In some embodiments, the polymer can be modified to resist cell attachment. In some embodiments, the modified polymer can be functionalized with a photo-activatable linker. Suitable photo-activatable linkers include, but are not limited to, 4-[p-azidosalicylamido]butylamine (ASBA), ABH, ANB-NOS, APDP, APG, BASED, NHS-ASA, SADP, SAED, SAND, SANPAH, and SPAD.

In some embodiments, the present invention provides systems, device and kits comprising: a substrate comprising one or more cell assay zones, each comprising a cell exclusion zone adjacent to a cell seeding zone, where the cell exclusion zone is created by the removal of material from the substrate area that defines the cell exclusion zone upon whose removal is allowed cell movement into the cell exclusion zone. In some embodiments, the removal of material from the substrate is achieved by a method selected from the group consisting of mechanical degradation, erosion, dissolution, irradiation, removal by shear forces, sonication, enzymatic degradation, magnetic degradation, electrical degradation, heating or cooling. In some embodiments heating or cooling of the polymer results in cell detachment without removing the polymer from the analytic zone. Upon returning the substrate to 37 degrees C. (normal incubation temperature) the polymer supports cell attachment and movement (e.g., migration or invasion) into the analytic zone.

In some embodiments, the present invention provides cell assay devices, systems and kits comprising: a substrate comprising one or more cell assay zones, each comprising a cell exclusion zone adjacent to a cell seeding zone, where the cell exclusion zone is modified to enable cell movement by a method selected from the group consisting of mechanical degradation, erosion, dissolution, irradiation, sonication, enzymatic degradation, magnetic degradation, electrical degradation, heating or cooling.

In some embodiments, the present invention provides methods of assaying cells comprising: providing a substrate comprising an array of cell assay zones each comprising a cell exclusion zone adjacent to a cell seeding zone, wherein the cell exclusion zone comprises a polymer that blocks adherence of cells to the substrate surface of the cell exclusion zone; seeding cells on the cell seeding zone; degrading the degradable polymer so that cells may adhere to the cell exclusion zone; allowing cells to migrate into the cell exclusion zone; and determining the relative number of cells in the cell exclusion zone.

In some embodiments, the present invention provides methods of assaying cells comprising: providing a substrate comprising an array of cell assay zones each comprising a cell exclusion zone adjacent to a cell seeding zone, wherein the cell exclusion zone comprises a polymer that blocks adherence of cells to the substrate surface of the cell exclusion zone; seeding cells on the cell seeding zone; modifying the polymer so that cells may adhere to the cell exclusion zone; allowing cells to migrate into the cell exclusion zone; and determining the relative number of cells in the cell exclusion zone.

In some embodiments, the present invention provides methods of assaying cells comprising: providing a substrate comprising an array of cell assay zones each comprising a cell exclusion zone adjacent to a cell seeding zone, wherein the cell exclusion zone comprises a polymer that blocks adherence of cells to the substrate surface of the cell exclusion zone; seeding cells on the cell seeding zone; functionalizing the polymer so that cells may adhere to the cell exclusion zone; allowing cells to migrate into the cell exclusion zone; and determining the relative number of cells in the cell exclusion zone.

In some embodiments, the present invention provides cell assay systems, devices and kits comprising: at least one magnetic particle; a first substrate comprising an array of cell assay zones; a second substrate comprising an array of magnets, wherein the first substrate and the second substrate are alignable so that the array of magnets is aligned with the array of cell assay zones and so that when the magnetic particles are added to the cell assay zones, the magnetic particles are attracted to the magnets thereby forming a cell exclusion zone within the cell assay zone. In some embodiments, the cells are inhibited from binding to the cell exclusion zone in the presence of the second substrate and the at least one magnetic particle. In some embodiments, the first substrate comprises a multiwell plate and the cell assay zones correspond to the bottoms of wells in the multiwell plate. In some embodiments, the second substrate is placed under the first substrate so that the magnetic particles are attracted to the magnets through the first substrate. In some embodiments, the at least one magnetic particle is selected from the group consisting of a magnetic beads and a magnetic disk.

In some embodiments, the present invention provides methods for assaying cells comprising: providing magnetic beads, a first substrate comprising an array of cell assay zones; and a second substrate comprising an array of magnets, wherein the first substrate and the second substrate are alignable so that the array of magnets is aligned with the array of cell assay zones and so that when the magnetic beads are added to the cell assay zones, the magnetic beads are attracted to the magnets thereby forming a cell exclusion zone within the cell assay zone; aligning the first substrate and the second substrate in the presence of the magnetic beads so that the magnetic beads are positioned in the cell exclusion zones; contacting the substrate so that the cells are inhibited from adhering; removing the second substrates so that the magnetic beads are removed from the cell exclusion zone thereby allowing the cells to adhere to the cell exclusion zone; allowing cells to migrate into the cell exclusion zone; and determining the relative number of cells in the cell exclusion zone.

In some embodiments, the present invention provides systems, device and kits comprising: a substrate comprising an array of cell assay zones each comprising a cell exclusion zone surrounded by a cell seeding zone; a mask configured to interface with the substrate, the mask having a array of apertures therein so that when the mask is placed in a parallel plane with the substrate the array of cell assay zones is aligned with the array of apertures, wherein the area of the aperture is larger than area of the cell exclusion zone and smaller than the cell seeding zone so that a portion of the cell seeding zone is exposed by the aperture; and polymeric inserts, wherein the polymeric inserts comprise an end that can contact the substrate to form the cell exclusion zone.

In some embodiments, the present invention provides systems, device and kits comprising: a substrate comprising an array of cell assay zones each comprising a cell exclusion zone surrounded by a cell seeding zone, wherein the cell exclusion zone comprises a polymer that inhibits adherence of cells to the cell exclusion zone.

In some embodiments, the present invention provides systems, device and kits comprising: at least one magnetic particle; a first substrate comprising an array of cell assay zones; a second substrate comprising an array of magnets, wherein the first substrate and the second substrate are alignable so that when the array of magnets is aligned with the array of cell assay zones and so that when the at least one magnetic particle is added to the cell assay zones, the magnetic beads are attracted to the magnets thereby forming a cell exclusion zone within the cell assay zone.

In some embodiments, the present invention provides methods of making a cell assay device comprising: providing a substrate and a mask having apertures therein, and forming analytic zones on said substrate that correspond to said apertures in said mask. In some embodiments, the methods further comprise providing a photoactivatable polymer and wherein said forming step comprises: applying said polymer to said substrate; aligning said mask on said substrate; and exposing said substrate to light so that said polymer is immobilized in zones on said substrate corresponding to said apertures in said mask. In some embodiments, the polymer is degradable. Suitable polymers include, but are not limited to, alginate, hyaluronic acid, starch glycogen, cellulose, chitin, xanthan gum, dextran, gellan gum, glucomannan, hydroxypropyl cellulose, hydroxypropylmethyl cellulose, carboxymethyl cellulose, carageenan, inulin, agarose, pullulan, and nucleic acids. In some embodiments, the photoactivatable polymer comprises a photoactivatable linker. Suitable photoactivatable linkers include, but are not limited to, 4-[p-azidosalicylamido] butylamine (ASBA), ABH, ANB-NOS, APDP, APG, BASED, NHS-ASA, SADP, SAED, SAND, SANPAH, SPAD. In some embodiments, the photoactivatable polymer is activated by exposure to ultraviolet light. In some embodiments, the methods further comprise providing magnetic particles and wherein said forming step comprises: applying said magnetic particles to said substrate; aligning said mask on said substrate; exposing said substrate to a magnetic field so that said magnetic particles align with said apertures. In still other embodiments, the forming step comprises exposing aligning said mask with said substrate and exposing said substrate to ultraviolet light through said substrate.

DESCRIPTION OF THE FIGURES

FIG. 17*a* shows a representative well following the PBS wash.

FIG. 17B shows a representative well after plates were returned to 37° C., 5% $CO_2$ for 48 hours.

FIG. 18A shows a schematic of a substrate where cells are centrally seeded with different agents. FIG. 18B shows a schematic of a substrate where the agent is centrally seeded and different cell lines are seeded on the edges.

DEFINITIONS

Figure 1:
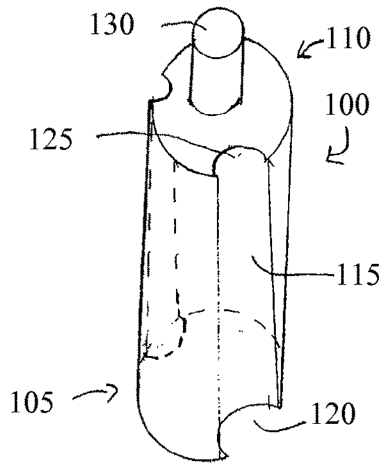
FIG. 1 depicts an insert for seeding cells in a multiwell plate.

As used herein, the term "substrate" refers to material capable of supporting associated assay components (e.g., assay regions, cell binding regions, mesogens that constitute the functional units of liquid crystals, cells, test compounds, etc.). For example, in some embodiments, the substrate comprises a planar (i.e., 2 dimensional) glass, metal, composite, plastic, silica, or other biocompatible or biologically unreactive (or biologically reactive) composition. In some other embodiments, the substrate comprises a porous (e.g., microporous) or structured (i.e., 3 dimensional) composition (e.g., sol-gel matrices). In some other embodiments, the substrate is a multiwell plate.

As used herein, the term "mesogen" refers to compounds that form liquid crystals, and in particular rigid, rodlike or disclike molecules that are components of liquid crystalline materials.

As used herein, "assay region", "assay zone" or "analytic zone" refers to a position on a substrate configured for the collection of data. In some embodiments, assay regions are configured to order mesogens. In other embodiments, assay regions are configured specifically to not order mesogens. In still further embodiments, assay regions are configured to provide two or more distinct regions (e.g., optically opaque regions and optically transparent regions, regions that are capable of ordering mesogens of liquid crystal (mesogens) and regions specifically lacking the ability to order mesogens placed on their surface, and combinations thereof).

As used herein, "array" refers to a substrate with a plurality of molecules (e.g., mesogens, recognition moieties) and/or structures (e.g., wells, reservoirs, channels, apertures and the like) associated with its surface in an orderly arrangement (e.g., a plurality of rows and columns). In another sense, the term "array" refers to the orderly arrangement (e.g., rows and columns) of two or more assay regions on a substrate.

The term "cell seeding region" or "cell seeding zone" as used herein, refers to a portion of an assay region or a substrate that is configured to provide an initial attachment site for one or more cell(s) of interest. In certain preferred embodiments, the cell seeding region comprises a depression in an assay region of the substrate.

As used herein, "taxis" refers to a response in which the direction of movement is affected by an environmental cue. It is clearly distinguished from a kinesis.

As used herein, "kinesis" refers to alteration in the movement of a cell, without any directional bias. Thus speed may increase or decrease (orthokinesis) or there may be an alteration in turning behavior (klinokinesis).

As used herein, "orthokinesis" refers to kinesis in which the speed or frequency of movement is increased (positive orthokinesis) or decreased (negative orthokinesis).

As used herein, the term "chemokinesis" refers to a response by a motile cell to a soluble chemical that involves an increase or decrease in speed (positive or negative orthokinesis) or of frequency of movement or a change in the frequency or magnitude of turning behavior (klinokinesis).

As used herein, the term "chemotaxis" refers to a response of motile cells or organisms in which the direction of movement is affected by the gradient of a diffusible substance. Differs from chemokinesis in that the gradient alters probability of motion in one direction only, rather than rate or frequency of random motion.

As used herein, the term "neoplasia" refers to abnormal new growth and thus means the same as tumor, which may be benign or malignant. This is now a general term used interchangeably with the term cancer, for more than 100 diseases that are characterized by uncontrolled, abnormal growth of cells. Neoplastic or cancerous cells can spread locally or through the bloodstream and lymphatic systems to other parts of the body.

As used herein, the term "migration" refers to the passing from one location to another. Used to describe the change in position of cells, microorganisms, particles or molecules.

As used herein, "cell movement" refers to any movement or change in shape of a cell including, but not limited to locomotion and cytoplasmic streaming, etc. As used herein, the term "proliferation" refers to the reproduction or multiplication of similar forms, especially of cells.

As used herein, "contraction" refers to a shortening or reduction in size of a cell. Typically associated with transduction of forces onto or into a substrate to which the cell is associated.

As used herein, the term "invasion" refers to the movement of cell(s) into a territory of differing composition. In particular it refers to the use of in vitro assay systems where cells are seeded on one substrate and they subsequently move into a 3 dimensional matrix. Ability to "invade" the 3 dimensional matrix is sometimes used as an indicator of malignant potential.

As used herein, the term "phototaxis" refers to movement of a cell or organism towards (positive phototaxis) or away from a source of light (negative phototaxis).

As used herein, the term "aerotaxis" refers to an organism's movement toward or away from oxygen as a reaction to its presence. The term is most often used when discussing aerobes (oxygen-using) versus anaerobes (which don't use oxygen).

As used herein, the term "osmotaxis" refers to movement of a cell or organism towards (positive osmotaxis) or away from (negative osmotaxis) a source of increased osmotic concentration of solutes.

As used herein, the term "immobilization" refers to the attachment or entrapment, either chemically or otherwise, of a material to another entity (e.g. a solid support) in a manner that restricts the movement of the material.

As used herein, the term "surface configured to orient mesogens" refers to surfaces that intrinsically orient mesogens (e.g., through anisotropic surface features such as obliquely deposited gold or rubbed proteins) and surfaces that are modified to orient liquid crystals by application of extrinsic structure or forces, including, but not limited to particles, electric fields, magnetic fields, or combinations thereof.

As used herein, the term "matrix" refers to any three dimensional network of materials, including, but not limited to, extracellular matrices, synthetic or biological polysaccharide matrices, collagen matrices, matrigel, polymer networks, soft microfabricated structures (e.g., from PDMS), gels of lyotropic liquid crystals, and matrices prepared from bacterial cell secretions. The materials of the matrices may be chemically crosslinked or physically crosslinked.

As used herein, the terms "material" and "materials" refer to, in their broadest sense, any composition of matter.

As used herein, the term "drug" refers to a substance or substances that are used to diagnose, treat, or prevent diseases or conditions. Drugs act by altering the physiology of a living organism, tissue, cell, or in vitro system that they are exposed to. It is intended that the term encompass antimicrobials, including, but not limited to, antibacterial, antifungal, and antiviral compounds. It is also intended that the term encompass antibiotics, including naturally occurring, synthetic, and compounds produced by recombinant DNA technology.

As used herein, the terms "home testing" and "point of care testing" refer to testing that occurs outside of a laboratory environment. Such testing can occur indoors or outdoors at, for example, a private residence, a place of business, public or private land, in a vehicle, as well as at the patient's bedside.

As used herein, the term "nanostructures" refers to microscopic structures, typically measured on a nanometer scale. Such structures include various three-dimensional assemblies, including, but not limited to, liposomes, films, multilayers, braided, lamellar, helical, tubular, pillar like and fiber-like shapes, and combinations thereof. Such structures can, in some embodiments, exist as solvated polymers in aggregate forms such as rods and coils. Such structures can also be formed from inorganic materials, such as prepared by the physical deposition of a gold film onto the surface of a solid, proteins immobilized on surfaces that have been mechanically rubbed, polymeric materials that have been mechanically rubbed, polymeric or metallic surfaces into which order has been introduced onto its surface by the use of micro and nanoabrasive materials (nanoblasting), high pressure water etching, and polymeric materials that have been molded or imprinted with topography by using a silicon template prepared by electron beam or other lithographic processes. Extrinsically structured anisotropic surfaces can also be formed by the placement of submicron to 10 μm sized particles (anisometric and/or isometric depending on the method used) and aligning or partially aligning the particles through the use of external fields (including, but not limited to, electric fields, magnetic fields, shear fields and/or fluid flow). It is also possible to create an aligned surface using mechanical transfer of organized or aligned particles (e.g., fabrication with a hydrophobic stamp containing the desired topography). The particles, when deposited onto the surface are organized or aligned such that mesogens contained within an overlying liquid crystal are aligned. These particles are displaced or reoriented when cells grow on the surface. Alternatively, the stamp can be made from friable materials that are transferred to the substrate upon contact with the substrate. Examples of such transferable materials include, but are not limited to, charcoal, chalk, soapstone, graphite, pumice, other easily fragmented and transferred materials and synthetic laminated material, prepared such that fracturing layers are designed into the material. Nanostructured substrates can also be fabricated using scanning probe methods, including atomic force microscopy and scanning tunneling microscopy, as well as x-ray lithography, micro/nanoabrasive methods, interferometric optical lithographic methods, and imprinting and embossing (including hot and cold embossing). Similarly, order can be introduced into a particle covered surface whereby particles are initially randomly positioned across a surface and an ordered pattern introduced by the selective removal of particles.

As used the term "multilayer" refers to structures comprised of two or more monolayers. The individual monolayers may chemically interact with one another (e.g. through covalent bonding, ionic interactions, van der Waals' interactions, dipole bonding, hydrogen bonding, hydrophobic or hydrophilic assembly, and steric hindrance) to produce a film with novel properties (i.e., properties that are different from those of the monolayers alone).

As used herein, the terms "self-assembling monomers" and "lipid monomers" refer to molecules that spontaneously associate to form molecular assemblies. In one sense, this can refer to surfactant molecules that associate to form surfactant molecular assemblies. The term "self-assembling monomers" includes single molecules (e.g., a single lipid molecule) and small molecular assemblies (e.g., polymerized lipids), whereby the individual small molecular assemblies can be further aggregated (e.g. assembled and polymerized) into larger molecular assemblies.

As used herein, the term "ligands" refers to any ion, molecule, molecular group, or other substance that binds to another entity to form a larger complex. Examples of ligands include, but are not limited to, peptides, carbohydrates, nucleic acids, antibodies, or any molecules that bind to receptors.

As used herein, the terms "organic matrix" and "biological matrix" refer to collections of organic molecules that are assembled into a larger multi-molecular structure. Such structures can include, but are not limited to, films, monolayers, and bilayers. As used herein, the term "organic monolayer" refers to a thin film comprised of a single layer of carbon-based molecules. In one embodiment, such monolayers can be comprised of polar molecules whereby the hydrophobic ends all line up at one side of the monolayer. The term "monolayer assemblies" refers to structures comprised of monolayers. The term "organic polymetric matrix" refers to organic matrices whereby some or all of the molecular constituents of the matrix are polymerized.

As used herein, the term "spectrum" refers to the distribution of light energies arranged in order of wavelength.

As used the term "visible spectrum" refers to light radiation that contains wavelengths from approximately 360 nm to approximately 800 nm.

As used herein, the term "ultraviolet irradiation" refers to exposure to radiation with wavelengths less than that of visible light (i.e., less than approximately 360 nm) but greater than that of X-rays (i.e., greater than approximately 0.1 nm). Ultraviolet radiation possesses greater energy than visible light and is therefore, more effective at inducing photochemical reactions.

As used herein, the term "in situ" refers to processes, events, objects, or information that are present or take place within the context of their natural environment.

As used herein, the term "liquid crystal" refers to a thermodynamic stable phase characterized by anisotropy of properties without the existence of a three-dimensional crystal lattice, generally lying in the temperature range between the solid and isotropic liquid phase.

As used herein, "thermotropic liquid crystal" refers to liquid crystals that result from the melting of mesogenic solids due to an increase in temperature. Both pure substances and mixtures form thermotropic liquid crystals.

"Lyotropic," as used herein, refers to molecules that form phases with orientational and/or positional order in a solvent. Lyotropic liquid crystals can be formed using amphiphilic molecules (e.g., sodium laurate, phosphatidylethanolamine, lecithin). The solvent can be water.

As used herein, the term "heterogeneous surface" refers to a surface that orients liquid crystals in at least two separate planes or directions, such as across a gradient.

As used herein, "nematic" refers to liquid crystals in which the long axes of the molecules remain substantially parallel, but the positions of the centers of mass are randomly distributed. Nematic liquid crystals can be substantially oriented by a nearby surface.

"Chiral nematic," as used herein refers to liquid crystals in which the mesogens are optically active. Instead of the director being held locally constant as is the case for nematics, the director rotates in a helical fashion throughout the sample. Chiral nematic crystals show a strong optical activity that is much higher than can be explained on the bases of the rotatory power of the individual mesogens. When light equal in wavelength to the pitch of the director impinges on the liquid crystal, the director acts like a diffraction grating, reflecting most and sometimes all light incident on it. If white light is incident on such a material, only one color of light is reflected and it is circularly polarized. This phenomenon is known as selective reflection and is responsible for the iridescent colors produced by chiral nematic crystals.

"Smectic," as used herein refers to liquid crystals which are distinguished from "nematics" by the presence of a greater degree of positional order in addition to orientational order; the molecules spend more time in planes and layers than they do between these planes and layers. "Polar smectic" layers occur when the mesogens have permanent dipole moments. In the smectic A2 phase, for example, successive layers show anti-ferroelectric order, with the direction of the permanent dipole alternating from layer to layer. If the molecule contains a permanent dipole moment transverse to the long molecular axis, then the chiral smectic phase is ferroelectric. A device utilizing this phase can be intrinsically bistable.

"Frustrated phases," as used herein, refers to another class of phases formed by chiral molecules. These phases are not chiral, however, twist is introduced into the phase by an array of grain boundaries. A cubic lattice of defects (where the director is not defined) exists in a complicated, orientationally ordered twisted structure. The distance between these defects is hundreds of nanometers, so these phases reflect light just as crystals reflect x-rays.

"Discotic phases" are formed from molecules that are disc shaped rather than elongated. Usually these molecules have aromatic cores and six lateral substituents. If the molecules are chiral or a chiral dopant is added to a discotic liquid crystal, a chiral nematic discotic phase can form.

"Thixotropic" as used herein, refers to materials that exhibit a stable form at rest but thin under shearing.

DETAILED DESCRIPTION OF THE INVENTION

The present invention relates to the fields of molecular biology, cellular biology, immunology, oncology, developmental biology, stem cell growth and differentiation, general laboratory science, and microbiology, and in particular to methods and compositions based on liquid crystal assays and other biophotonic assays for detecting and quantifying the presence of cells, cell secretory products including polypeptides and enzymes, microorganisms (including but not limited to viruses, bacteria, fungi and parasites) and particulate matter on a substrate. The ability to correlate an output signal with cell number makes the devices of the present invention widely useful for assays of cell adhesion as well as cell proliferation, cell death and cellular differentiation.

In some preferred embodiments, the cell assay devices, systems, kits, and methods of the present invention have improved dynamic range and sensitivity as compared to previous assays, such as those described in U.S. Pat. No. 7,018,838 and co-pending U.S. application Ser. No. 10/579,118, each of which are incorporated herein by reference in its entirety. The increase in dynamic range was achieved by making the mask aperture of the assay system overlap with the zone where the cells are seeded. This is a surprising result because it was previously thought that detection of cells from the cell seeding zone of the assay would interfere or bias the results of detection of cells that had migrated into the cell exclusion zone of the assay.

In other preferred embodiments, the present invention provides new assay systems that do away from the need to use silicone inserts to create cell exclusion zones and cell seeding zones on the assay substrate. In some embodiments, the new assay systems use a variety of different polymer systems to create cell exclusion zones and cell seeding zones on the assay substrate. In other embodiments, magnetic bead systems are used to create cell exclusion zones and cell seeding zones on the assay substrate. These embodiments, provide unexpected advantages over the previously described assay systems in that the new systems are easier to fabricate, less prone to user error, and easier to scale up for high throughput applications.

I. Assay Systems

The cell migration assays of the present invention comprise a substrate. The substrate preferably comprises a surface or plurality of surfaces on which the assay is conducted. In preferred embodiments, the substrate is a multiwell plate, such as an 8, 16, 48, 96, 386 or more well plate. In other embodiments, the substrate is a solid surface formed from a polymeric material such as plastic, polystyrene, or the like that can be divided into a series of cell assay zones. In some embodiments, the substrate comprises one or more microchannels for delivery of assay reagents to the cell assay zones, while in other embodiments, the cell assay zones form a well in the substrate material.

Preferably, the substrates comprise a series of cell assay zones in an array. The cell assay zones in turn comprise a cell seeding zone and a cell exclusion zone. In preferred embodiments, the cell seeding zone is a material or treated surface (for example, collagen treated surface) to which cell can adhere. In preferred embodiments, cells are added to the cell seeding zone and allowed to adhere, and are prevented from adhering to the cell exclusion zone. Upon removal of the inhibition to access to the cell exclusion zone of the assay, cells are free to migrate into the cell exclusion zone where they can be detected as described in detail below.

A variety of methods are contemplated for forming cell seeding zones and cell exclusion zones. Some systems are described in U.S. Pat. No. 7,018,838 and co-pending U.S. application Ser. No. 10/579,118, each of which are incorporated herein by reference in its entirety. Some of these embodiments are described in FIGS. 1-13 and are useful with the present invention.

Figure 3:
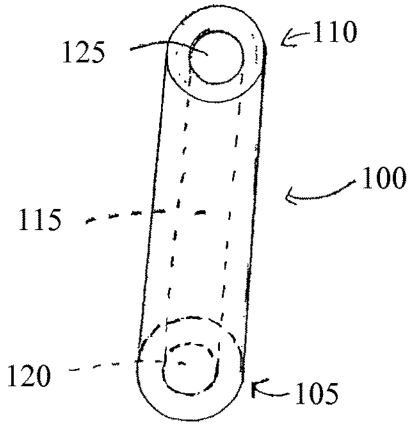
FIG. 3 depicts an insert for seeding cells in a multiwell plate.
Figure 4:
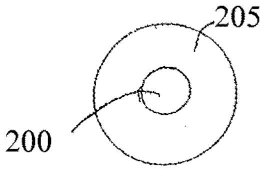
FIG. 4 depicts the seeding pattern obtained using the insert depicted in FIG. 3.
Figure 5:
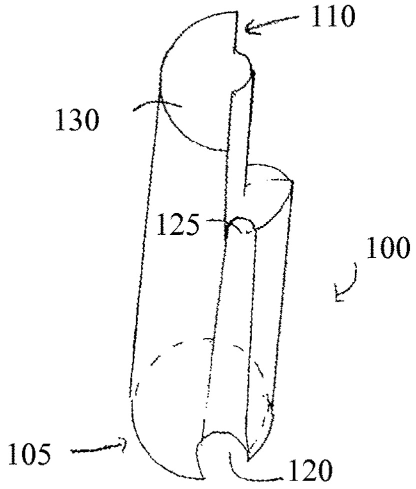
FIG. 5 depicts an insert for seeding cells in a multiwell plate.

Referring to FIGS. 1-10, some embodiments of the assay systems, kits and methods of the present invention comprise inserts and other devices for seeding cells in a particular predetermined area in a well in a multiwell well plate. In some embodiments, the cell seeding insert is formed from a pliable material. In some embodiments, the cell seeding insert is formed from a polymeric material. In some embodiments, the cell seeding insert is formed from an elastomeric material. In particularly preferred embodiments, the cell seeding inserts are formed from silicone or PDMS. In some embodiments, the insert is formed from a rigid material. In still further embodiments, the insert comprises both rigid and pliable materials that could be formed by lamination, co-extrusion, overmolding, or mechanically affixed processes. In some embodiments, the cell seeding inserts are configured to be insertable into or integrated through treatment of the bottom of wells of 6, 12, 24, 96, 384 or 1536 well plates. In some embodiments, when the cell seeding insert 100 is inserted into a well in a multiwell plate (not shown), the sides of the cell seeding insert contact the sides of the well in the multiwell plate. Referring to FIGS. 1 and 5, a cell seeding insert 100 of the present invention is preferably cylindrical in shape, although the shape can be varied to correspond to virtually any shape of well (square, rectangular, hexagonal, oval, etc.). In preferred embodiments, the cell seeding insert has a first end 105 and a second end 110. In some embodiments, the cell seeding insert has at least one channel therein. In some embodiments, the channel extends from an opening 120 in the first end of the cell seeding insert to an opening 125 in the second end of the cell seeding insert so that a fluid can be delivered from the first end of the cell seeding insert to the second end of the cell seeding insert when the cell seeding insert is inserted in a well of a multiwell plate (not shown). In some embodiments, the cell seeding insert 100 further comprises a projection 130 extending from the second end 110 of the cell seeding insert 100. In some embodiments, the projection 130 is cylindrical in shape (i.e., as shown in FIG. 1), although in other embodiments, the projection can be any desired shape as a square, triangle, rectangle, star, or crescent, as shown in FIG. 5.

FIG. 3 provides yet another embodiment of a cell seeding insert of the present invention. Referring to FIG. 3, in some embodiments, the cell seeding insert 100 is cylindrical in shape and has a first end 105 and second end 110. In some embodiments, a channel 115 extends from the first end 105 of the cell seeding insert 100 to the second end 110. The first and seconds ends 105 and 110 each have openings 115 therein defining the ends of the channel 115. As above, in some embodiments, the cell seeding insert is formed from a pliable material. In particularly preferred embodiments, the cell seeding inserts are formed from silicone or PDMS. In some embodiments, the cell seeding inserts are configured to be insertable into 6, 12, 24, 96, 384 or 1536 well plates. In some embodiments, when the cell seeding insert 100 is inserted into a well in a multiwell plate (not shown), the sides of the cell seeding insert contact the sides of the well in the multiwell plate.

Figure 18:
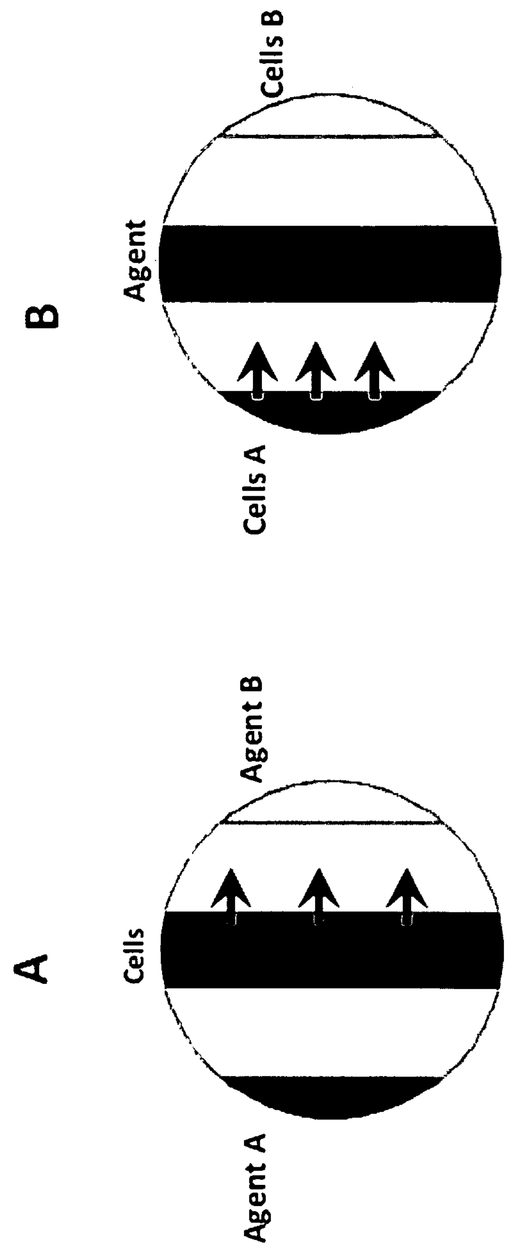
FIG. 18 shows a triple seeding insert used in some embodiments of the present invention.

An additional cell seeding insert is described in FIG. 18. FIG. 18 describes a triple seeding insert. The insert (e.g., silicone insert) fits into a multi well plate and seals off two liner section of the well bottom forming three separate linear chambers. FIG. 18A shows a schematic of a substrate where cells are centrally seeded with different agents. FIG. 18B shows a schematic of a substrate where the agent is centrally seeded and different cell lines are seeded on the edges.

In some embodiments, one or more of the cell seeding inserts (e.g., the cell seeding inserts described in FIGS. 1, 3, and 5) are inserted into one or more wells of a multiwell plate so that either the projection on the second end of the insert (see, e.g., FIGS. 1 and 5) or the second end (see, e.g., FIG. 3) contacts the bottom of the one or more wells of the multiwell plate. In some embodiments, cells in media are then seeded in the one or more wells via the channels in the inserts. In preferred embodiments, the cells seed in a predetermined area in the well defined as the area that is not contacted by the projection or second end of the insert. In other words, contacts of the projection or second end of the inserts with the bottom of the well define an area in which cells are excluded when cells are introduced into the well. The cells seed in the area of the well where there is no contact between the projection of second end of the insert and the well bottom.

Figure 2:
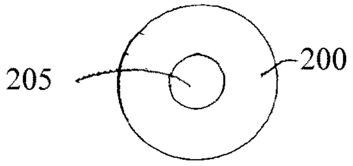
FIG. 2 depicts the seeding pattern obtained using the insert depicted in FIG. 1.
Figure 6:
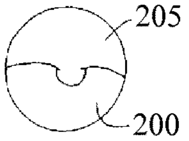
FIG. 6 depicts the seeding pattern obtained using the insert depicted in FIG. 5.

Examples of the seeding patterns obtainable with the cell inserts described in FIGS. 1, 3, and 5 are provided in FIGS. 2, 4, and 6, respectively. FIGS. 2, 4, and 6 depict the seeding pattern in the bottom of a well. Referring to FIG. 2, when the cell seeding insert of FIG. 1 is utilized, the cells are seeded in a predetermined annular area 200 and excluded from the circular area 205 in the center of the well. Referring to FIG. 4, when the cell seeding insert of FIG. 3 is utilized, the cells are seeded in a predetermined circular area 200 in the center of the bottom of the well and excluded from the annular area 205*a* the periphery of the bottom of the well. Referring to FIG. 6, when the cell seeding insert of FIG. 5 is utilized, the cells are seeded in a predetermined crescent-shaped area 200 and excluded from the area 205 in the bottom of the well.

Figure 7:
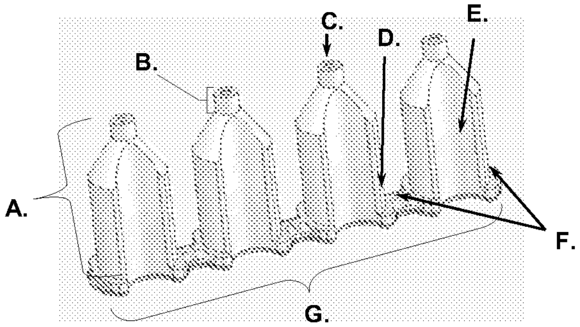
FIG. 7 depicts a strip of four cell seeding inserts.

Another cell seeding insert is depicted in FIG. 7. Referring to FIG. 7, a strip of four cell seeding inserts is provided. Alternatively, strips of 6, 12, 16 or more cell seeding inserts may be provided. The cell seeding insert preferably comprises one or more insert tips (A), each comprising a cell exclusion tip (B). The cell exclusion tip preferably seals with the well bottom and forms a restricted area in which cells are prevented from seeding. On one end, the cell exclusion tip comprises a sealing surface (C) that contacts the well bottom. In some embodiments, the sealing surface preferably has therein a recessed dimple that aids in sealing to the bottom of a well. As shown the cell seeding insert also has therein a seeding channel (E) running the length of the insert to facilitate adding a solution containing cells to a well in a multiwell plate. In some embodiments, where strips of inserts are provided, the inserts are separated by a hinge region D. The hinge region has therein a slot on the underside (not shown) that reduces strain on the insert backbone (G) of the strip from one insert tip to the next. The hinge can be severed to allow the insert tips to function as four individual inserts rather than as a strip. In some embodiments, the inserts further comprise a removal tool pocket (F). The removal tool pockets are preferably angled pockets designed to interact with a removal tool (described in more detail below). The pockets provide a gap between the top of the well and the bottom of the insert backbone. The insert backbone (G) is a sheet of pliable material (preferably silicone) that connects the individual inserts.

In use, the inserts are placed into the wells of a 96-well plate, oriented with the cell exclusion tips downward. Sufficient pressure is applied to each insert to induce a seal between the sealing surface of the cell exclusion tips and the bottom of the well. Biological cells, suspended in media, are introduced into the wells via the seeding channels on the side of the insert tips by using a single or multi-channel pipette. As the cells settle to the bottom of the well, they are restricted from the center of the well by the cell exclusion tip and permitted to access to an annular region of the well. The seeded plate is incubated for a period of time to allow adhesion of the cells to the plate bottom. When the inserts are removed, the adhered cells are situated only in an annular ring, while the center region of the well remains void of cells. During further incubation, the biological cells are permitted to migrate into the central, analytical zone of the well. The migration can either be monitored visually by using a microscope, or by staining the cells and then measuring absorbance of the stain by using a plate reader. In other embodiments, liquid crystals are used to visualize cell migration as explained in more detail below.

The latter method was used to seed HT1080 cells and to observe their migration. Briefly, 50,000 cells were delivered to wells of a 96-well plate that was populated with inserts. The plate was incubated for 4 hours at 37° C. and 5% humidity to allow adherence of cells. Following incubation, the inserts were removed and the wells were washed with media to remove any non-adhered cells. The wells then received 100 μl of media (MEM containing 10% FBS) and the plate was incubated for an additional 21 hours to allow cell migration. The cells were then stained with a fluorescent dye, Calcein AM, and the pattern of fluorescence signal was observed by using an Axiovert microscope fitted with a FITC filter.

In some further preferred embodiments, the present invention provides a series of inserts in the form of a strip. In some embodiments, the individual inserts are detachably connected to one another so that individual inserts can be removed from the strip. For example, in some embodiments, the inserts extends from a planar strip that has perforations between each insert.

In still other preferred embodiments, the invention provides for the engineering of a specific spatial zone in individual wells of the multiwell plate (e.g., 6, 12, 24, 96, 384 or 1536 wells) that blocks cellular attachment during the initial cell seeding period (for example, 4-12 hours) but later permits cell attachment and migration. In some embodiments, the cell exclusion zone comprises a polymer that blocks or otherwise prevents cell adhesion to the surface of the substrate comprising the cell exclusion zone. In some embodiments, the polymers may be printed in the cell assay zone of the substrate. The polymer may be printed in any shape, such as a circle, semicircle, oval, crescent, square, rectangle, etc. It will be recognized that cells may adhere to the polymer, but removal of the polymer along with the cells creates an area on the surface of the substrate that is free from cells. In other embodiments, the surface of the cell assay substrate comprising the cell exclusion zone is blocked by the use of a magnetic particle such as a disc or magnetic beads. In other embodiments, the cell exclusion zone initially allows cell attachment but through subsequent manipulation, cells detach from the exclusion zone leaving the periphery of the well populated by cells. Accordingly, in some embodiments, the present invention provides assay substrates, each comprising a call exclusion zone adjacent to a cell seeding zone, where said cell exclusion zone is modified to enable cell migration by a method selected from the group consisting of mechanical degradation, erosion, dissolution, irradiation, sonication, enzymatic degradation, magnetic degradation, electrical degradation, heating or cooling.

Figure 8:
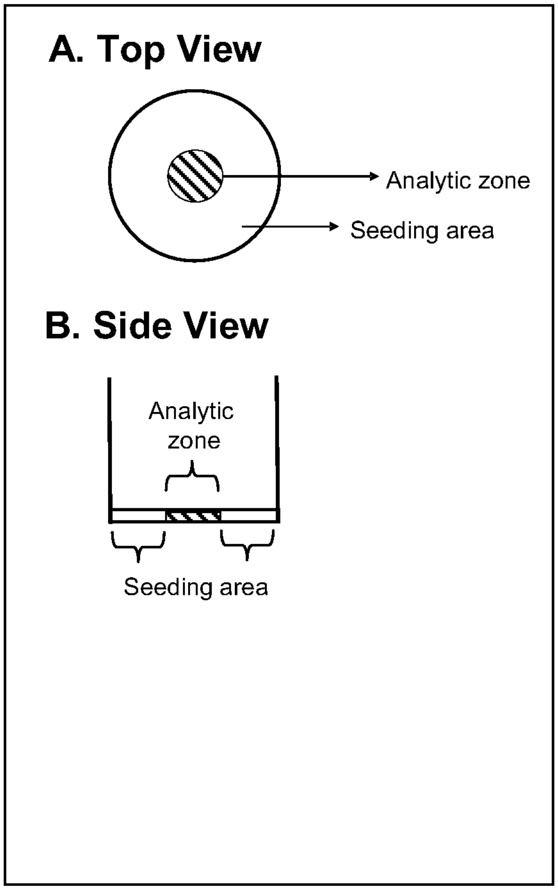
FIGS. 8A and 8B provide a schematic depiction of top (A) and side (B) views of multiwell plate well bottom having an analytic zone (cross hatched) and seeding areas (clear).
Figure 9:
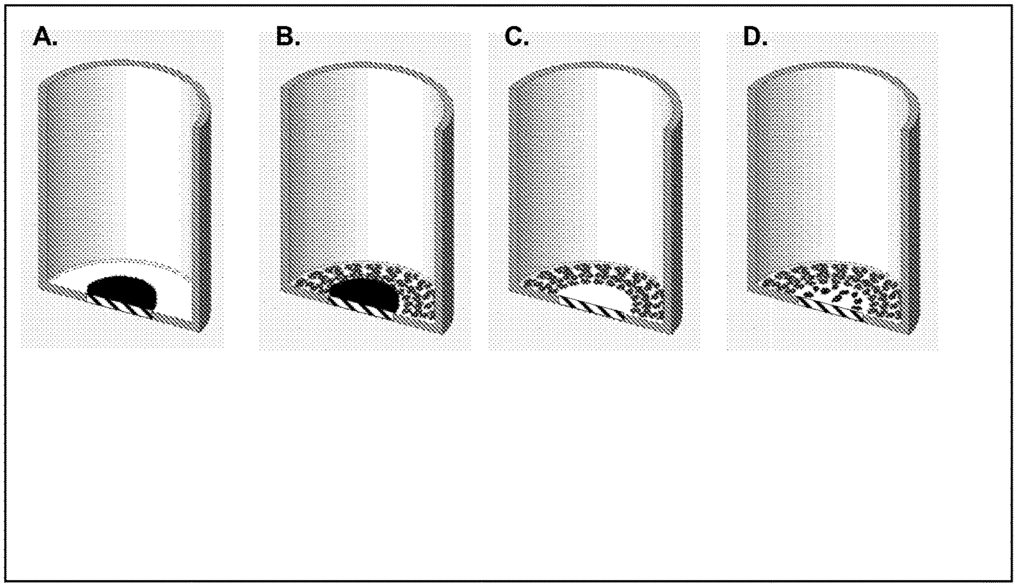
FIGS. 9A-D provide a schematic depiction of cells seeded into wells have an analytic zone made of dissolvable polymer. The four images represent cut-away views of wells such as those in a 96-well tissue culture plate. Panel A depicts a central area (i.e., analytic zone) on the well bottom onto which a dissolvable polymer has been printed. Cells are delivered to the well and allowed to adhere; attaching in the annular region but not in the central, polymer coated area (Panel B). When the polymer dissolves (Panel C), the cells then migrate into the analytic zone (Panel D).
Figure 10:
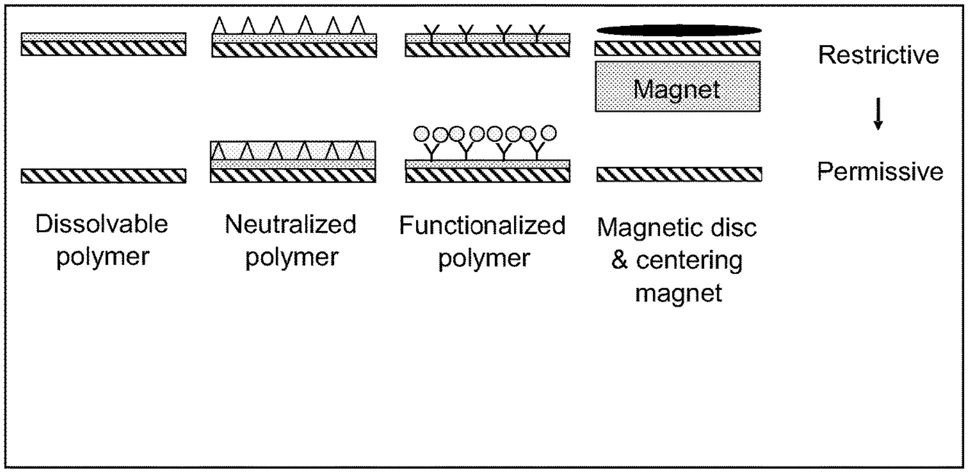
FIG. 10 provides a schematic depiction of four methods of forming g a cell exclusion zone on a substrate using a dissolvable polymer, a neutralizable polymer, a functionalized polymer, and magnetic disc and centering magnet.

These embodiments have advantages over the polymeric insert in ease of fabrication, decreased cost of goods, and in making the assay ergonomically simpler to perform. These embodiments are depicted in FIGS. 8, 9, and 10 provide schematic depictions of these embodiments.

In some embodiments, the assay devices comprise one or more cell assay zones comprising a cell seeding zone and a cell exclusion zone, wherein the cell exclusion zone comprises a polymer that inhibits cell adherence to the cell exclusion zone. In some preferred embodiments, the cell assay zones are arranged in an array on the substrate. In some particularly preferred embodiments, the substrate is a multiwell plate and the cell assay zones are located on the bottom surface of the wells in the plate, preferably one cell assay zone per well.

A variety of different polymers find use in the present invention. In some embodiments, the polymer is degradable. In some preferred embodiments, the applied polymer is non-toxic to cells, resists initial cell adhesion and dissolves in a 4-10 hour time frame. The cells are seeded into a well and incubated for 4-6 hours to allow adhesion in the permissible areas. Next, the well is washed to remove non-adhered cells, seeding media and any dissolved polymer, and fresh media is added. The majority of the polymer is dissolved by that time point with the remainder totally removed by a few additional hours of incubation. Once the polymer has dissolved, the cells can readily migrate into the analytic zone. Although many materials can be utilized in the invention, preferred materials would be those that dissolve in a non-linear fashion with time, including as a relatively abrupt event at around 6-10 hours. In some embodiments, the polymer is a biopolymer. In some embodiments, the biopolymer is selected from the group consisting of polysaccharide carbohydrates and nucleic acid. In some embodiments, the polysaccharide carbohydrates is selected from the group consisting of alginate, hyaluronic acid, starch glycogen, cellulose, chitin, xanthan gum, dextran, gellan gum, glucomannan, and pullulan. In some embodiments the nucleic acid is selected from the group consisting of ribonucleic acid, single stranded deoxyribonucleic acid (ssDNA), and double-stranded deoxyribonucleic acid (dsDNA). In some embodiments, the dsDNA contains a specific nucleotide sequence that is recognized and subsequently cleaved by a restriction endonuclease. In some preferred embodiments, the degradable polymer is degradable by enzyme, for example, hyaluronidase, cellulase, alginase, restriction enzyme, DNase, etc. In some preferred embodiments, the degradable polymer is hydrolysable upon exposure to an aqueous solution. These classes of materials include materials that undergo degradation and hydrolysis, such as polymers containing esters. Other examples of such degradable polymers include, but are not limited to: polyelectrolyte multilayers that incorporate polymers that undergo hydrolysis such as multilayered polyelectrolyte assemblies fabricated from sodium poly(styrene sulfonate) (SPS) and three different hydrolytically degradable polyamines (see Zhang et al., LANGMUIR 22 (1): 239-245 (2006); bioerodible polymeric material based on n-butyl hemiester of [poly(maleic anhydride-alt-2-methoxyethyl vinyl ether)] (PAM14)(Piras et al., J. Nanosci. Nanotech. 6 (9-10): 3310-3320 (2006)); in situ-gelling, erodible N-isopropylacrylamide copolymers, as described by Lee and Vernon, Macromol. Biosci. 5 (7): 629-635 (2005); polymers prepared from poly(lactic acid) and poly[(lactic acid)-co-(glycolic acid)], as described Alexis, Polymer Int'l 54 (1): 36-46 (2005); polymers prepared from gelatin-sodium carboxymethylcellulose interpenetrating polymer networks, as described by Rathna and Chatterji, J. Macromol. Sci. Pure Appl. Chem. A40 (6): 629-639 (2003); hyaluronic acid, gels prepared from hyaluronic acid and pluronics, such as described Kim and Park, J. Controlled Release 80 (1-3): 69-77 (2002).

In some embodiments, the polymers are photoactivatable. In some preferred embodiments, the photoactivatable polymers comprise a photoactivatable linker, e.g., the polymer is functionalized with a photoactivatable linker. Suitable photoactivatable linkers include, but are not limited to, 4-[p-azidosalicylamido]butylamine (ASBA), ABH, ANB-NOS, APDP, APG, BASED, NHS-ASA, SADP, SAED, SAND, SANPAH, and SPAD.

In other embodiments, the polymer is an oligonucleotide. In some embodiments, the oligonucleotide is modified by pegylation and is a pegylated oligonucleotide. In some embodiments, the oligonucleotide comprises a sequence recognized by a restriction enzyme (i.e., restriction site). When the oligonucleotide is attached to a surface, for example by a photoactivatable linker, the oligonucleotide can be released from the surface by exposure to the appropriate restriction enzyme. In general, the oligonucleotide may be from 10 to 200 bases in length. The oligonucleotide may be either single or double-stranded. In general, the sequence and overall length of the oligonucleotide can vary and will be determined based on the restriction enzyme as well as the ability of the restriction enzyme to work under reaction conditions that do not interfere with the adherence of mammalian cell monolayers. In some embodiments, the oligonucleotide comprises a random sequence that is digestible upon treatment with deoxyribonuclease I (DNase I) enzyme. In some embodiments, the oligonucleotides are be modified for attachment to peptide sequences via an amide linkage. In some embodiments, these peptide sequences are sequences that stimulate cell signaling or promote adhesion such as the three amino acid RGD sequence found in the extracellular matrix protein fibronectin or to a poly-L-lysine moiety that is used as a tissue culture well surface treatment to promote cell attachment. Such modifications would necessarily remain attached to the well bottom to make the surface more attractive or permissive to cell migration once the oligo has been digested with the nuclease. In some embodiments, the oligonucleotide is modified by the attachment of multi-arm PEG groups (e.g., 4 or 6 arms). However, if the physical properties of such a PEGylated oligo would not make it amenable for nanodeposition, the oligo may be prepared with an amino modification to allow for subsequent coupling of the multi-arm PEG to the oligo using carbodiimide chemistry after the oligo has been dispensed and adsorbed to the well surface. Once treated with an enzyme, cleavage must effectively remove the PEGylated portion of the oligo.

In some preferred embodiments, a polymer composite that is partially composed of magnetic particles is utilized. The polymer/particle composite blocks the analytic zone during cell seeding and then forces generated by a magnet would be used to accelerate the dissolution/disruption of the composite. In this way the disruption of the analytic zone could be initiated at the desired 6-10 hour time point.

In further embodiments, heat labile polymers are utilized to form the cell exclusion zone on the substrate. In these embodiments, light (patterned on the analytic zone) is used to cause the dissolution of the polymer that has been applied to the pre-determined exclusion zone. Cells are then seeded and allowed to adhere in permissive areas. Then, with a mask in place to protect the cells from exposure, a light is used to heat the polymer a fraction of a degree or a few degrees so that it undergoes a phase transition and dissolves. In preferred embodiments, the light is an infrared light. In some embodiments, the polymers further comprise 1) a chromophore that undergoes degradation or strongly absorbs light upon exposure to certain wavelengths of light or 2) beads that strongly absorb light and thus promote localized heating to trigger dissolution of the polymer. In preferred embodiments, temperature sensitive acrylamide polymers are utilized. Examples of polymers that undergo dissolution upon heating near 37° C. include, but are not limited to, erodible N-isopropylacrylamide copolymers, as described by Lee and Vernon, Macromol. Biosci. 5(7): 629-635 (2005) and Ankareddi and Brazel, Int'l J. Pharmaceutics 336(2): 241-247 (2007); cellulose acetate butyrate-pH/thermosensitive polymer, as described in Fundueanu et al., Euro. J. Pharm. Biopharm. 6 (1): 11-20 (2007). Examples of dyes and pigments useful in the present invention include, but are not limited to, Orange OT, azobenzene, and Dye Blue.

In still further embodiments of the present invention, the cell exclusion zone is formed as a degradable/dissolvable laminated structure in which the upper layer of the laminate does not degrade and does not permit cell attachment. In preferred embodiments, the lower layer of the laminate is dissolvable and/or degradable. The dissolution of the bottom layer causes detachment of the protective upper layer from the surface—leading to an abrupt unmasking of the analytic zone in the 6-10 hour time frame. In some embodiments, detachment of the upper layer could be promoted at the desired time by convection, use of magnetic beads embedded in it, or exposure to light. In preferred embodiments, the laminated structure is fabricated by a two-step printing process in the well.

In other embodiments, the cell exclusion zone is formed from a polymer that resists cell adhesion but that can be made adhesion-permissive by addition of a neutralizing reagent at the start of the assay. In this embodiment, the cell exclusion zone is established by applying a polymer to a pre-determined area on the well bottom in a multi-well plate. In preferred embodiments, the polymer is non-toxic to cells and resists initial cell adhesion. The cells are seeded into the well and incubated for 4-6 hours to allow adhesion in the permissible areas. Next, the well is washed to remove non-adhered cells and a reagent is added that neutralizes the polymer (i.e., the polymer persists in the well but its surface would be activated by addition of the second reagent). The present invention is not limited to the use of any particular polymer or activating agents. In preferred embodiments, the polymer prevents cell attachment prior to exposure to a polyelectrolyte, but promotes cell attachment after exposure to the polyelectrolyte. For example, ethyleneglycol-terminated surfaces and perfluorocarbon-terminated surfaces resist cell attachment, but can adsorb polyelectrolytes that will facilitate protein adsorption and cell attachment. As a further example, polyamines adsorb to cell-resistant ethyleneglycol surfaces. Jiang at al., Langmuir 18(4): 1131-1143 (2002). In this example, an oligoethylene glycol-terminated region is defined as the exclusion zone (e.g., by printing, spotting) on the surface of the well. The cells are seeded, but do not attach to the ethylene glycol terminated regions. To initiate the migration of cells onto the exclusion region, a small amount of a polyamine is added to the cell culture medium. This polyamine adsorbs to the oligoethyleneglycol-terminated regions, promotes protein adsorption and permits subsequent cell migration into the exclusion zone.

In further embodiments, the cell exclusion zones on a substrate are formed by printing (establishing) the cell exclusion zone using a polymer that resists cell adhesion but that can be made adhesion-permissive by addition of a functionalizing reagent at the start of the assay. In this embodiment, the analytic zone is established by applying a polymer to a pre-determined area on the well bottom in a substrate, such as a multi-well plate. In preferred embodiments, the polymer is non-toxic to cells and resists initial cell adhesion. The cells are seeded into the well and incubated for 4-6 hours to allow adhesion in the permissible areas. Next, the well is washed to remove non-adhered cells and a reagent added that would functionalize the polymer (i.e., the polymer persists in the well but its surface functionality would change by addition of the second reagent). Examples of this include, but are not limited to, a polyethylene glycol (PEG) functionalized to specifically bind fibronectin and/or collagen (such as biotinylated antibodies that bind avidinylated fibronectin). In these embodiments, the surface is functionalized at the start of the assay to encourage cell migration. A wide range of recognition events are envisaged in preferred embodiments of the invention, including using nucleic acids to bring fibronectin/collagen to the surface. Examples of functionalized PEGs include, but are not limited to, end-functionalized poly (ethylene glycol) layers, et al., Langmuir 18(20): 7482-7495 (2002) and NHS-functionalized PEG. By using amino-biotin, it is straightforward to attach the biotin to the PEG-terminus using procedures known to those skilled in the art. The biotinylated PEG resists protein attachment and cell seeding. Upon introduction of a fusion protein comprised of a biotin binding domain (from avidin) and a fibronectin or collagen, the surface is transformed into one that promotes cell attachment.

In still other embodiments, a magnetic bead system is utilized to form the cell exclusion zones on the substrate. In these embodiments, a magnetic stand is utilized to secure magnetic beads in the pre-determined cell exclusion zone. Cells are seeded and the substrate, such as a multi-well plate, is then removed from the magnetic stand. The beads disperse and unmask the cell exclusion zone thus permitting migration of cells into the zone. Alternatively, a metallic (in preferred embodiments, 2.0 mm diameter) disc that is controlled by a jig with magnets provides the cell exclusion zone during cell seeding. Removal of the discs (using magnets), after cell attachment is complete, permits cell migration into the zone.

In some embodiments, the present invention provides methods for creating an analytic zone in which an opaque mask defines the analytic zone at the onset of the study, remains in place for the duration of the study and is used at the end of the study to analyze activity in the analytic zone.

In some embodiments, the analytic zone is formed by placing a magnetic disc, magnetic beads, or magnetic polymer into the wells. A mask, with 96 apertures corresponding to the array of wells in the plate, is then applied to the bottom of the plate. The plate, with mask adhered, is then placed on a stand that provided 96 magnetic areas that also corresponding to the array of wells in the plate and thus in the mask. Raised areas on the magnetic stand fit into the apertures of the mask and direct the magnetized particles in the plate wells into position. The cells are seeded into the well and incubated (while on the magnetic stand) for 4-6 hours to allow adhesion in the permissible areas. The plate with mask in place is then lifted from the magnetic stand and the magnetic particles, non-adhered cells and seeding media is removed from the wells. The well is washed and cells re-fed with fresh media. Once the magnetic particles are removed, the cells migrate into the analytic zone. Following incubation, the amount of cells that have migrated into the analytic zone is examined by viewing through the mask apertures.

In some embodiments, the analytic zone is formed by removing cells from the central portion of the well. In some embodiments, cells are seeded into the plate wells and incubated for 4-6 hours to allow adhesion over the entire well bottom. Then, with a 96-aperture mask in place, the seeded plate is exposed, from the bottom, to a light source emitting UV light. The mask defines the analytic zone by allowing the UV light to ablate those cells that were exposed via the apertures. The mask protects those cells adhered in the annular region of the well from UV exposure. After UV treatment, the cells in the annular region migrate into the center of the well. The mask remains in place throughout the procedure to provide the best possible registration of the mask aperture with the analytic zone.

In some embodiments, the analytic zone is formed by use of a UV-activatable exclusion reagent that is non-permissive for cell attachment. In other embodiments, the UV-activatable reagent is permissive and after cells are seeded in the region, an enzyme removes the reagent and thus the cells. The exclusion reagent is added to the well, a mask aligned to the plate bottom, and the plate exposed to UV light. UW activation of the reagent in the unmasked areas, i.e., exposed through the mask apertures, attaches the reagent to the well bottom, while the masked areas remain "tissue culture" treated. Cells are seeded in the wells and incubated for 4-6 hours to allow adhesion in the permissive areas of the well bottom. Then, the tethered exclusion reagent is detached from the well bottom, for example by introduction of an enzyme that cleaves a portion of the reagent and renders the formerly non-adhesive area now cell adhesion permissive. Cells then migrate into the area and could be viewed and/or quantitated through the same mask apertures that were used previously to create the analytic zone. In preferred embodiments, the exclusion reagent is a degradable polymer comprising a photoactivatable linker. Suitable degradable polymers and photoactivatable linkers are described above.

It can be appreciated that the assay plate, although described here as a 96-well plate, could consist of any number of multiple wells including but not limited to 6, 12, 24, 48, 96, 384, 1536, etc.

In further embodiments, the present invention provides masks for use with multiwell plates. In some embodiments, the masks are designed to cover a predetermined portion of one or more wells of a multiwell plate. In some preferred embodiments, the masks are used in conjunction with the cell seeding inserts described above. In some embodiments, the masks are used to cover a predetermined portion of a well, wherein the predetermined portion corresponds to an area where cells have been seeded in a well in a multiwell plate. In such a system, the migration of cells from the predetermined, masked portion of the well to an unmasked portion of the well can be assayed simply by determining the presence of cells in the unmasked portion of the well. It will be further recognized that the masks can be used in methods, systems, and kits which utilize a variety of detection methods, including but not limited to calorimetric, fluorimetric, light scattering, liquid crystal, densitometric, and microscopic assays. The masks can also be utilized in methods, systems, and kits that include the cell seeding inserts and substrates comprising cell assay and exclusion zones described above.

Accordingly, in some embodiments, the masks of the present invention are formed from an opaque material or material that otherwise restricts the transmission of light. In preferred embodiments, the masks have one or more apertures, or openings, therein. In some embodiments, the apertures are arranged in an array. In particularly preferred embodiments, the array of apertures in the mask corresponds to the array of cell assay zones on a substrate, such as a multiwell plate. In use, the mask is placed adjacent to the substrate, between the substrate and a source of radiation such as ultraviolet radiation, visible light, or infrared radiation. The mask is preferably positioned so that the radiation passes through the mask apertures and irradiates at least the cell exclusion zone on the assay substrate. In preferred embodiments, the aperture area of the mask exceeds the area of the cell exclusion zone so that the cell seeding zone is also at least partially irradiated. In preferred embodiments, where the cell exclusion zone and mask apertures are circular, the diameter of the mask aperture is greater than the diameter of the cell exclusion zone so that a portion of the cell exclusion zone is exposed to radiation. It will readily be envisioned that when the cell exclusion is a different shape than circular, such as square, rectangular, crescent, or oval shaped, the aperture can be sized so that areas of the apertures exceeds the area of the cell exclusion zone to expose a portion of the cell seeding zone to the assay. Surprisingly, it has been found that exposure of a portion of the cell seeding zone to excitement radiation during the detection step of the assay increases the dynamic range and sensitivity of the assay for cells that have migrated into the cell exclusion zone when automated detection systems such as plate readers are utilized for the detection step. The present invention is not limited to any particular mechanism of action. Indeed, an understanding of the mechanism of action is not necessary to practice the instant invention. Nevertheless, it is believed that signal generated from cells in the cell seeding zone that have not migrated sensitize the detector, such a plate reader, so that signal from low numbers of cells that have migrated can be detected. In some preferred embodiments, the diameter of the mask aperture is from about 0.1% to about 20%, 0.5% to about 20%, 1% to about 20%, 1% to about 15%, 1% to about 10%, 1% to about 5%, 5% to about 20%, or 5% to about 15% larger than the diameter of the cell exclusion zone. In other preferred embodiments, the diameter of the mask aperture is from about 0.1 mm, 5 mm, 10 mm, 20 mm, or 50 mm to about 100 mm or 200 mm larger than the diameter of the cell exclusion zone. With the use of some multiwell plate readers it is possible to spatially restrict the light sensor to specific locations on the bottom of the well making the use of a mask unnecessary for readout of the assay.

Figure 11:
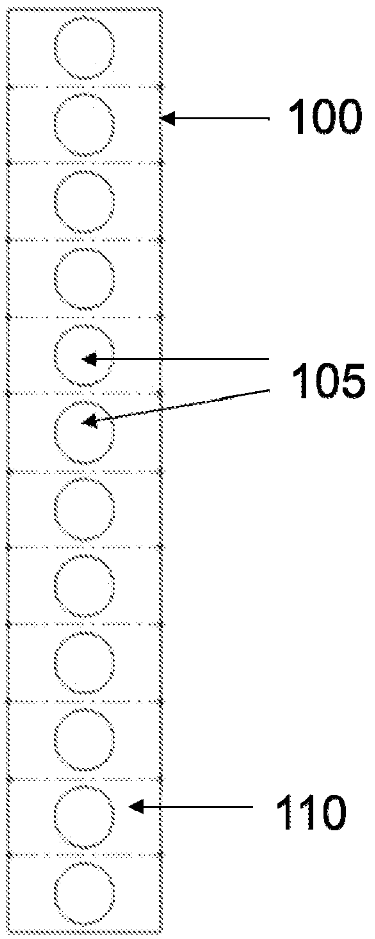
FIG. 11 depicts a mask for a 96-well plate.

Referring to FIG. 11, a mask (100) of the present invention is provided. In some embodiments, the mask has therein a series of openings (105) corresponding to a predetermined area within the well of a multiwell plate. In some embodiments, the mask (100) comprises a surface (110) having an adhesive so that the mask can be fixed to a multiwell plate. In some embodiments, the mask comprises a series of strips that correspond to rows of wells in a multiwell plate. FIG. 11 is a depiction of one such strip. In some embodiments (not shown), the strips are attached to one another, for example, by perforations in the material of the mask, so that the strips may be separated and used separately to mask individual wells or rows of wells in a multiwell plate or be left together and used to mask all of the wells of a multiwell plate. In some embodiments, the masks are formed from plastic. In other embodiments, the mask is made of paper or paper with a plastic coating. In some embodiments the mask is created by printing or painting of the external surface of the bottom of the well. It will be recognized that the openings 105 in the mask 100 can be virtually any shape, including, but not limited to circles, squares, rectangles, triangles, stars, annular rings (e.g., donut shaped with an annular opening surrounding a solid center connected to the rest of the masked by a small extension), and so forth. In some embodiments, the openings are preferably configured to correspond in size to the circular area 205 in FIG. 2. In such a system, the movement of cells seeded in the predetermined annular area 200 of FIG. 2 into the predetermined circular area 205 can be determined.

In still further embodiments, the mask 100 has one or more priming apertures associated with and separate from the openings 105. The aperture is preferably located so that it exposes cells initially seeded in the well of the multiwell plate. The aperture is preferably large enough to provide a signal that exceeds the threshold level of detection of plate reader, for example, when cells are labeled with a fluorescent probe and exposed to the appropriate wavelength of excitation radiation. This embodiment is especially useful when plate readers are used for signal detection and/or quantitation because by providing for a threshold level of signal via the aperture, the migration of one or a few cells into the predetermined, unmasked area can be detected, even if the number of cells and signal obtained therefrom would otherwise be beneath the threshold level of detection.

In other embodiments (not shown), the mask has one or more fluorescent tags associated with and separate from the apertures. The tags may be adhered or printed on the mask. The fluorescent signal emitted from the tags is preferably large enough to provide a signal that exceeds the threshold level of detection of the plate reader acting similarly to the priming apertures described above.

In other embodiments (not shown), the mask is sized to correspond to the size of a multiwell plate so that the mask can be attached to the underside (i.e., the side on which the bottom of the wells are located) of a multiwell plate. In some, the mask includes clips so that it can be attached to a multiwell plate. In other embodiments, the multiwell plate comprises clips for attachment of the mask. In still other embodiments, the multiwell plate comprises channels into which the mask can be inserted. In other embodiments the multiwell plate and the mask are attached by friction-fitting. In preferred embodiments, the mask includes openings corresponding to a predetermined portion of the bottoms of the wells in the multiwell plate. It will be recognized that the openings in the mask can be virtually any shape, including, but not limited to circles, squares, rectangles, triangles, stars, annular rings (e.g., donut shaped with an annular opening surrounding a solid center connected to the rest of the masked by a small extension), and so forth. In some embodiments, the openings are preferably configured to correspond in size to the circular area 205 in FIG. 2. In such a system, the movement of cells seeded in the predetermined annular area 200 of FIG. 2 into the predetermined circular area 205 can be determined. The masks can be formed from any suitable material, including, but not limited to, plastic, paper, cardboard, and plastic-coated paper or cardboard.

Figure 12:
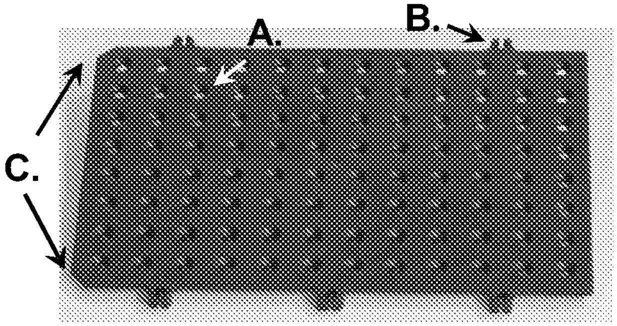
FIG. 12 depicts features of a mask for a 96-well plate.

Another mask of the present invention is depicted in FIG. 12. In preferred embodiments, the masks are used for cell migration assays. The mask preferably comprises of a sheet of material that fits onto the bottom of a 96-well tissue culture plate ("plate"). The mask includes 96 chamfered apertures configured in an 8×12 array that correspond to the centers of the wells in the plate. The locations of the apertures also match the locations of the insert tips that populate the plate. The chamfers function to maximize light transmission and eliminate shadows when the plate and mask assembly is placed on a light source. The purpose of the mask is two-fold. First, it blocks any signal, i.e., emitted or transmitted light, from the biological cells that are seeded in the annular region. Second, it permits the passage of signal from cells that reside in the analytical zone. The outcome is that only cells that have migrated from the annular region into the analytic zone will be detected.

Figure 13:
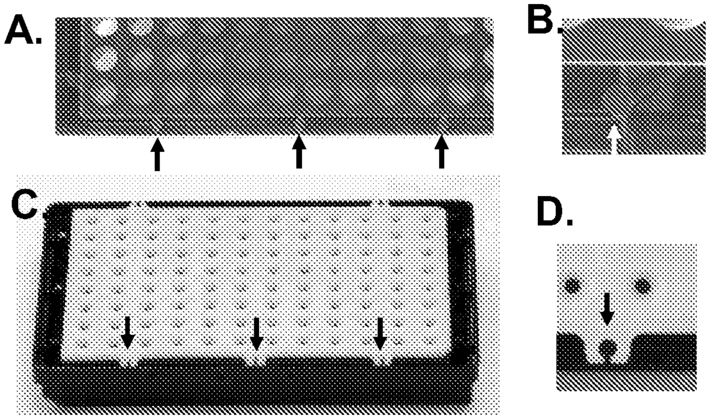
FIGS. 13 A-D depict alignment of the mask apertures with the assay zones of the plate.
Figure 14:
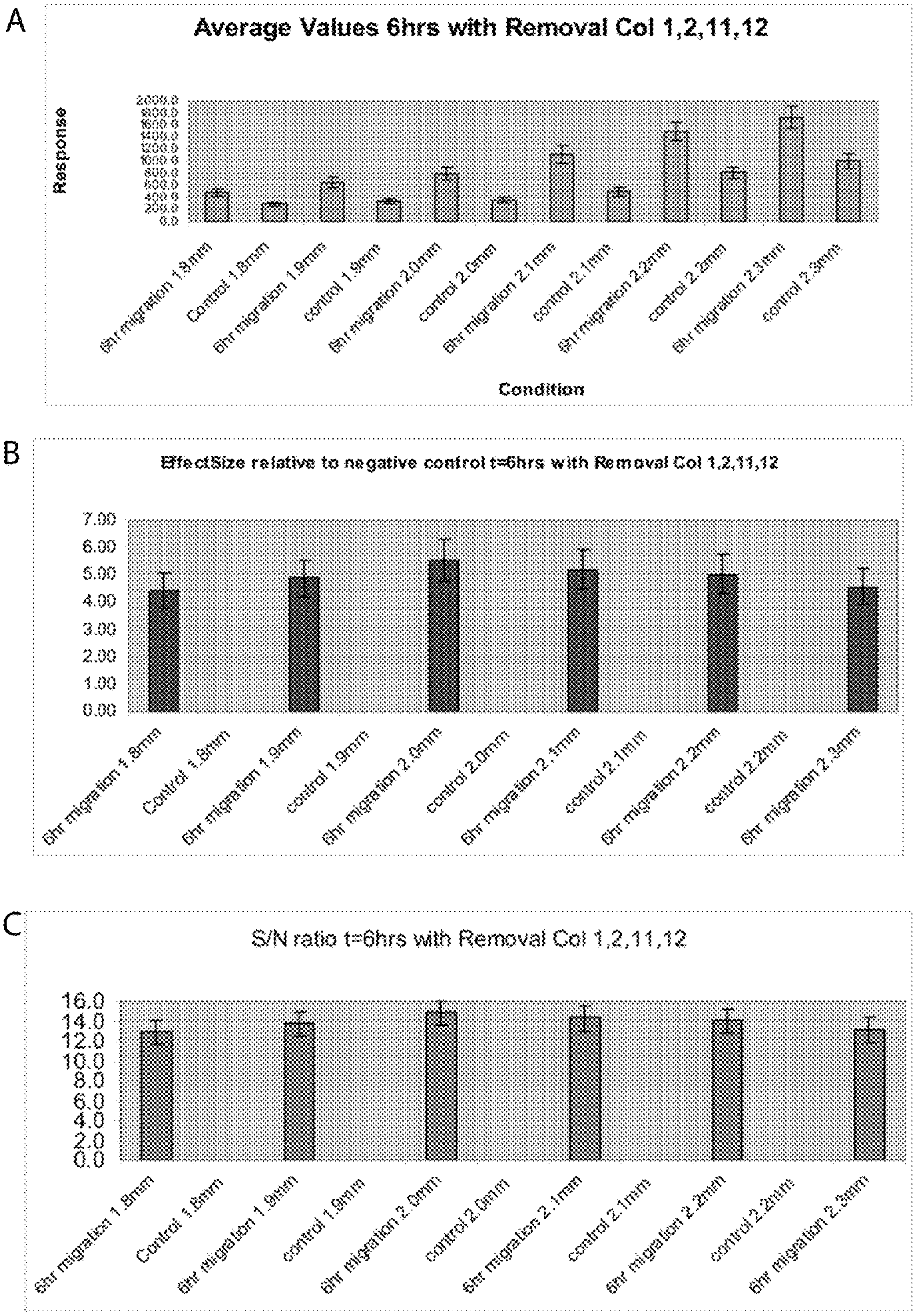
FIGS. 14 A-C provides data for experiments with different mask aperture sizes after 6 hours of cell migration.
Figure 15:
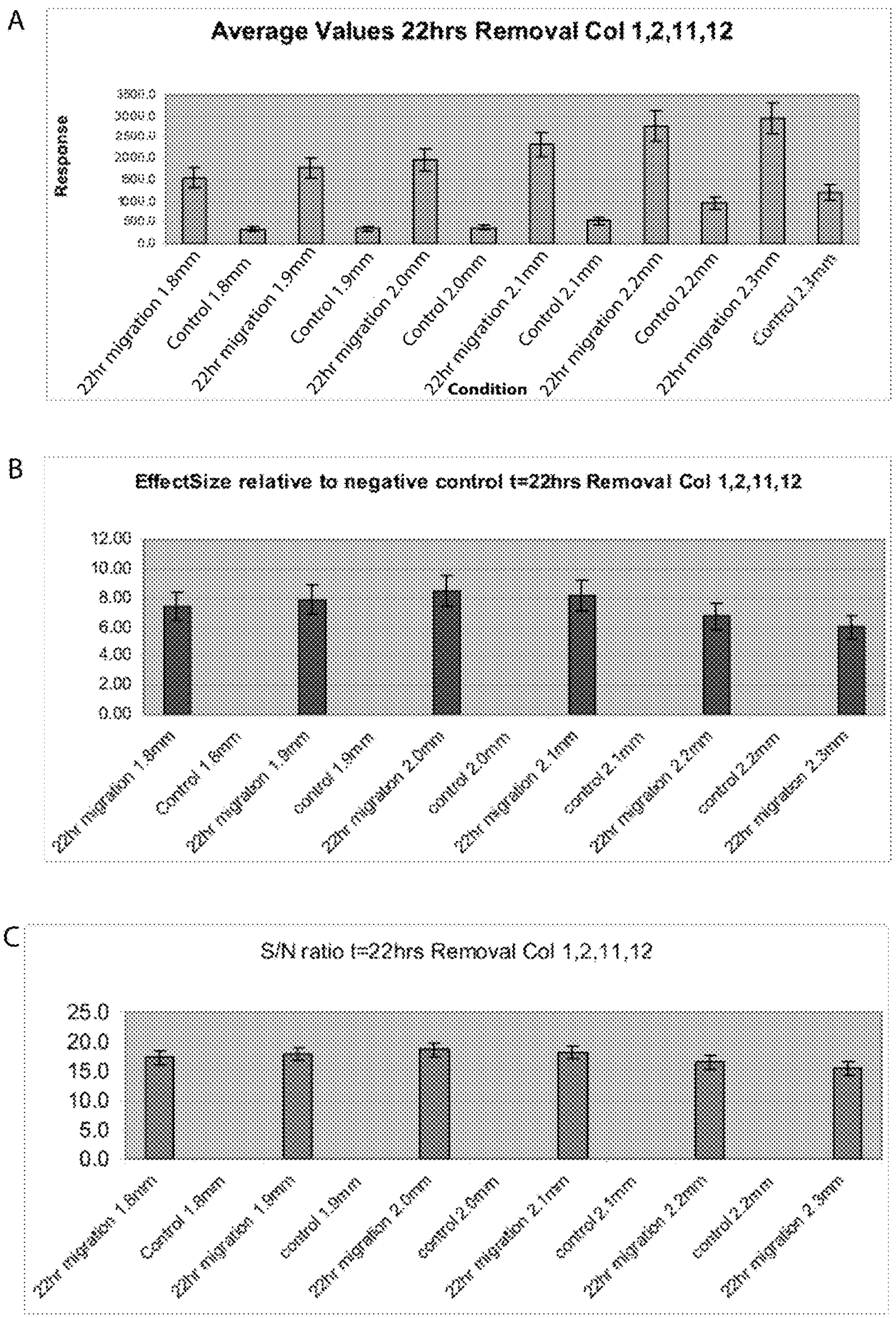
FIG. 15 A-C provides data for experiments with different mask aperture sizes after 22 hours of cell migration.
Figure 16:
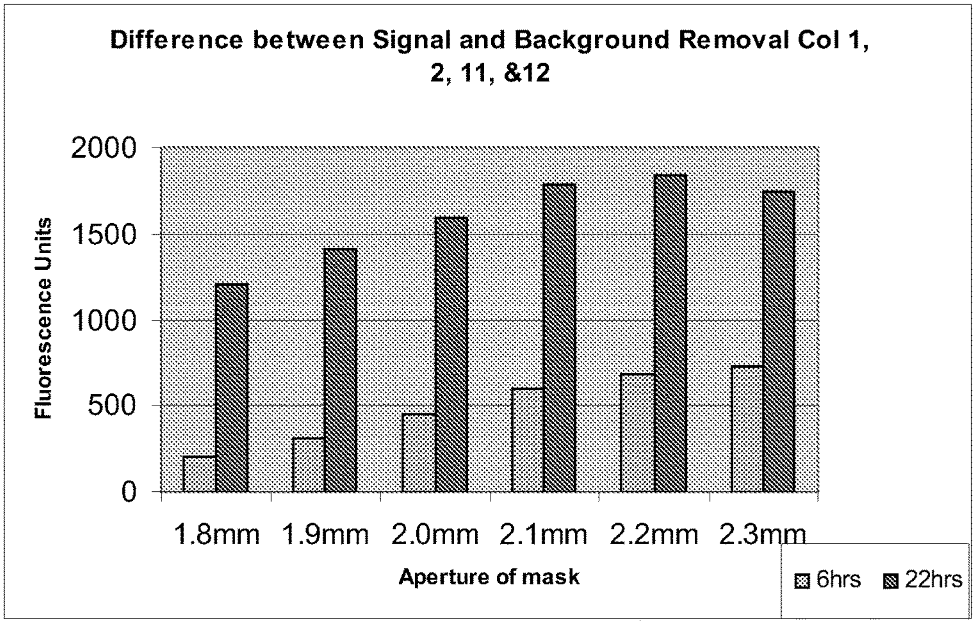
FIG. 16 provides the difference between signal and background for experiments with different mask aperture sizes.

Referring to FIGS. 12 and 13 A, B, C and D, the optical mask comprises of an opaque sheet containing 96 chamfered apertures (FIG. 12 at A). The apertures are configured in an 8×12 array that corresponds with the wells of the 96-well plate. The mask features five asymmetrically-placed attachment lugs (FIG. 12 at B) that are used to secure the mask to the bottom of the plate. The holes in the lugs fit over bosses on the bottom of the plate, establishing proper alignment. The lugs are slotted to permit them to expand slightly and engage the boss securely. The mask also features two angled corners (12 at C) that mimic the profile of the plate bottom. This provides a visual cue for proper mask orientation. When the mask is fitted to the plate bottom, FIGS. 13A-D, the apertures align with the analytic zone in each well as established by the cell seeding inserts.

II. Detection Systems

A variety of detection systems may be utilized to detect migration of cells from the cell seeding zone on the substrate into the cell exclusion zone on the substrate. Suitable detection systems include, but are not limited to, light microscopes, stereoscopes, flatbed scanning devices, and plate readers. In preferred embodiments, plate readers are utilized for detection. In preferred embodiments, the detection systems include a radiation source for irradiating labeled cells with an appropriate wavelength of excitation radiation for the label selected. Commercially available plate readers that may be used according to the present invention include, but are not limited, to those available from Nalge Nunc International Corporation (Rochester, N.Y.), Greiner America, Inc. (Lake Mary, Fla.), Akers Laboratories Inc., (Thorofare, N.J.), Alpha Diagnostic International, Inc. (San Antonio, Tex.), Biotek Instruments, Inc., (Winooski, Vt.), Tecan U.S. (Durham, N.C.), and Qiagen Inc. (Valencia, Calif.).

In some embodiments, the assayed cells are labeled before or after cell seeding and migration. The present invention is not limited to the use of any particular label. In some preferred embodiments, fluorescent dyes are used as labels. Preferred dyes include, but are not limited to, Calcein AM, 7-AAD, Acridine orange, BCECF, FDA, CDCFDA, CFDA, Coelenterazine, Fluo-3 AM, Rhod-2 AM, Fura-2 AM, Indo 1 AM, Quin-2 AM, DAPI, Hoechst 33258, and Hoechst 33342. In other embodiments, the fluorescent dye is bound to a compound, such as an antibody, that binds to an epitope on the surface of the cell. Suitable dyes include fluoroscein isothiocyanate (FITC), green fluorescent protein, yellow fluorescent protein, and red fluorescent protein. In other embodiments, label-free detection is accomplished using by using liquid crystals to report the cells.

In some embodiments (for example, cell migration or movement assays), the plate reading device is configured to sample multiple regions within in a given assay region. For example, the plate reader can be configured to provide multiple circular readouts within a circular region defined by a well of a multiwell plate. Thus, the presence of cells can be detected in regions that are remote from a central cell seeding area. As another example, the plate reader is configured to provide readouts in concentric circles originating from a central cell seeding region. In this embodiment, the number of cells within each successive concentric circle provides information as to the extent of migration (for example, in response to a test compound). The area under the curve for the signal from each successive concentric circle can be measured and plotted (signal vs. zone) to provide an analysis of strength of response to a test compound.

In other embodiments, the plate reading device is configured asymmetrically sample a well or other assay region, for example, the right or left side of a central cell seeding zone. It is contemplated that such asymmetric sampling will yield data that distinguishes chemotaxis from chemokinesis. For example, if the number of cells in the right and left regions is equal, the compound is chemokinetic. If the cell signal is strongest in the region with the highest amount test compound, then the compound is chemotactic. It will also be recognized that the plate reader can be configured as described above so that the multiple discrete regions are read within a given assay region. Chemokinesis is indicated by randomly distributed cells, while chemotaxis is indicated by an increased number of cells in sample areas oriented closer to a test compound source as opposed to areas more remote from a test compound source.

It will also be recognized that the present invention provides an assay system comprising a plate reading device and an assay substrate and mask as described in detail above, wherein the plate reading device, assay substrate and mask are configured so that light provided from the plate reading device which is passed through at least one surface of the assay substrate is detected by a detection unit of the plate reading device. Suitable detecting units include CCDs, photodiodes and photomultiplier tubes.

In other embodiments, imaging systems (e.g., array reading systems and gel readers) may be utilized that image the entire plate or a portion thereof (e.g., individual wells) at once. The data obtained from such systems is then processed to provide information on individual assay areas with the plates or wells. Such imaging systems can preferably utilize optical imaging devices such as CCDs or other imaging devices such as magnetic resonance imagers.

In other embodiments, liquid crystals are used to image cells on the assay substrates. In some preferred embodiments, the cell adhesion and cell proliferation assays are performed on nanostructured substrates or substrates onto which structure is introduced by the seeding or decoration of the surface with nano- to micro-sized particles that order the LC layers applied thereto.

While not being limited to any particular mechanism or theory, the present invention contemplates that in these assays, the area occupied by a cell is roughly equivalent to a planar surface as it would not orient a LC placed over its surface. Therefore, the number of cells present on a substrate will be proportional to the surface area covered by the cells. It is contemplated that the exact relationship between surface area occupied by a given number of cells is dependent on the cell type and line used and the culture conditions employed.

In some preferred embodiments of the present invention, the area occupied by cells attached to an ordered substrate is characterized by a non-aligned (i.e., disordered) area of the liquid crystal. The area occupied by cells is thus quantifiable using a variety of methods. In preferred embodiments, the assay device is analyzed using cross polars in conjunction with a CCD, photodiode or photomultiplier. With this system, the increased amount of light transmitted through the disordered areas can be analyzed. In further preferred embodiments, specific wavelengths of light are used in conjunction with thin films of liquid crystals to report the area occupied by cells.

In still other preferred embodiments of the invention, a liquid crystalline substrate is prepared such that the presence of a cell attached to the surface of the liquid crystalline substrate leads to a change in the optical appearance of the substrate.

Substrates suitable for the cell adhesion, quantification, proliferation and migration assays include, but are not limited to, substrates having rubbed protein surfaces, rubbed polymeric surfaces (e.g., tissue culture polystyrene), ordered polymeric substrates formed by micromolding of lithographically created masters, oblique deposition of gold films, and nano- to micro-sized particles seeded onto the surface that are ordered upon initial deposition using a nanostamper or negative nanostamper or particulate matter that is randomly seeded onto a surface and subsequently ordered by motive forces, exemplified by, but not limited to electric fields, magnetic fields and fluid flow. An additional substrate suitable for cell adhesion and proliferation assays is a liquid crystalline substrate. The liquid crystalline substrate is preferably prepared from a low molecular weight liquid crystal, a polymeric liquid crystal, a lyotropic or thermotropic liquid crystal, or a composite of liquid crystal and polymer, including biological polymers such as those that comprise the extracellular matrix.

The plate readers may be used in conjunction with the LC assay devices described herein and also with the lyotropic LC assays described in U.S. Pat. No. 6,171,802, incorporated herein by reference. In particular, the present invention includes methods and processes for the quantification of light transmission through films of liquid crystals based on quantification of transmitted or reflected light.

The present invention is not limited to any particular mechanism of action. Indeed, an understanding of the mechanism of action is not required to practice the present invention. Nevertheless, it is contemplated that ordered nanostructured substrates impart order to thin films of liquid crystal placed onto their surface. These ordered films of liquid crystal preserve the plane of polarized light passed through them. If the liquid crystal possesses a well-defined distortion—such as a 90 degree twist distortion—then the liquid crystal will change the polarization of the transmitted light in a well-defined and predictable manner. It is further contemplated that ordered films of liquid crystal differentially absorb (relative to randomly ordered films of liquid crystal) specific wavelengths of light.

In some embodiments of the present invention, the amount of target molecule or molecules bound to a sensing surface of an LC assay device (i.e., a surface decorated with a recognition moiety) increases with the concentration/amount of target molecule present in a sample in contact with a sensing surface. In preferred embodiments, the amount of bound target molecule changes the degree of disorder introduced into a thin film of liquid crystal that is ordered by nature of the underlying nanostructured sensing substrate. In some embodiments, the degree of order present in a thin film of liquid crystal determines the amount of light transmitted through the film when viewed through crossed polars. In other embodiments, the degree of order present in a thin film of liquid crystal determines the amount of light transmitted through the film when viewed using specific wavelengths of light. In still other embodiments, the reflectivity of an interface to a liquid crystal can change with the orientation of the liquid crystal. Therefore, in some embodiments, oblique illumination of the LC assay device is utilized with collection and analysis of reflected light being performed.

Accordingly, the present invention contemplates the use of plate readers to detect light transmission through an LC assay device when viewed through cross or parallel polars, the transmission of light through an LC assay device illuminated with a suitable wavelength of light, or reflection of light (i.e., polarized light or non-polarized light of specific wavelengths) from the surface of an LC assay device. In particularly preferred embodiments, plate readers are provided that are designed to be used in conjunction with LC assays. Other embodiments of the present invention provide modified commercially available readers such as ELISA readers and fluorometric readers adapted to read LC assays.

Non-limiting examples of the plate readers adapted for use in the present invention may be found in WO 03/019,191, which is herein incorporated by reference. In preferred embodiments, two polarizing filters are placed in the optical pathway of the plate reader in a crossed or parallel polar configuration. One filter is placed on the emission side of the light path prior to passing through the sample while a second polarizing filter is placed on the analyzing side of the light path after light has passed through the sample but before it is collected by a sensing devise such as a photodiode, a photomultiplier or a CCD. An ordered liquid crystal in the LC assay device preserves the plane of polarization and the amount of light reaching the light gathering and sensing device is markedly attenuated when viewed through cross polars or markedly accentuated when viewed through parallel polars. Random organization of the liquid crystal of the LC assay device does not preserve the plane of polarization and the amount of light, passing through crossed polars, reaching the light collecting and sensing device is relatively unaffected. Accordingly, in preferred embodiments, the binding of target molecules by the recognition moieties in an LC assay device introduces disorder into the overlying thin film of LC that increases with the amount of bound target molecule. In other preferred embodiments, the presence of a cell on an ordered region introduces disorder into the overlying LC. In other embodiments, specific bandpass filters are placed on the excitation side of the light path before light encounters the sample as well as on the emission side of the light path (after light has passed through or is reflected by the sample but before reaching the light collecting and sensing device (e.g., photodiode, photomultipier or CCD). This configuration is useful for quantifying both reflected and transmitted light.

The present invention also provides LC assay devices configured for use in the plate reader. In preferred embodiments, the LC assay device is formatted or arrayed according to the dimensions of standard commercially available plates (e.g., 24, 96, 384 and 1536 well plates). In some embodiments, the LC assay device comprises a surface (e.g., a substrate with recognition moieties attached) that is of proper external dimensions to be accurately fit into a given commercial reader. In some embodiments, the substrate contains uniform topography across its surface, in other embodiments, the substrate contains a gradient of topographies across its surface whereas in yet other embodiments regions of topography are limited to discrete regions that correspond to areas read out by commercial plate readers. In some embodiments, the orientational order of the LC is determined by using a dichroic dye or fluorescence dye dissolved within the LC in combination with absorbance-based or fluorescence-based reporting.

III. Cell Assays

The following sections further describe various embodiments of the present invention. The present invention is not intended to be limited however to the following embodiments. Indeed, one skilled in the art will be readily able to apply and adapt the disclosed embodiments directed to detecting cell migration, adhesion, proliferation, and cytological features for use in applications in other fields and disciplines.

The present invention provides devices and methods for the determination of cell number in combination with cell proliferation and cell adhesion assays. As such, the present invention provides a single platform for multiple cell assays, including, but not limited to, adhesion, migration, proliferation, invasion, death, differentiation and contraction assays. The devices and methods of the present invention provide distinct advantages over and complement methods including direct cell counting using microscopy and a hemocytometer or automated cell counting devices (e.g., a Coulter counter); calorimetric assays that utilize substrate conversion by intracellular enzymes (e.g., MTT assays); direct calorimetric assays based on extraction of dyes (and subsequent quantification) after initial vital staining of cells; fluorometric assays based on enzymatic conversion (e.g., Calcein AM-molecular probes that provides a fluorometrically converted substrate for intracellular esterases; fluorometric assays based on DNA binding (e.g. Hoechst dyes); calorimetric or fluorometric assays based on identification of intracellular correlative indicators of cell proliferation such as detection of Proliferating Cell Nuclear Antigen (PCNA); BRDU labeling of DNA and examining by microscopy; radiometric assays based on incorporation of tritiated thymidine; and flow cytometry with propidium iodide labeling.

Additionally, the present invention provides methods that allow quantification of movement of cells in response to cytoactive agents as well as under control conditions. Compounds that promote cell migration may be chemotactic (e.g., compounds that stimulate directed cell migration in response to a gradient) or chemokinetic (e.g., compounds that stimulate cell migration that is not gradient or directionally dependent) agents. Additionally, inhibition of cell migration may be quantified. It is contemplated that adhesion is indicative of a change in functionality of the cell. Indeed, adhesion represents a first essential step in cell migration. Adhesion is also a requirement for survival and subsequent proliferation of anchorage dependent cell types such as fibroblasts and epithelial cells. For example, adhesion documents an essential change in leukocytes that participate subsequently in diapedesis and is an essential component of wound healing.

It is contemplated that proliferation is indicative of normal growth and/or replacement of effete cells in the maintenance of homeostasis. Proliferation is also a fundamental aspect of neoplasia and an essential component of wound healing, ontogeny, inflammation and the immune response. Adhesion, migration, differentiation and proliferation are fundamental cell behaviors that are modulated by soluble factors (e.g., cytokines, chemokines, neuropeptides, neurotrophins, polypeptide growth factors) as well as by the extracellular matrix constituents (e.g., collagens, laminin, vitronectin, fibronectin) and influenced by other cells and their products in the environment. Examining how these processes are modulated in vitro provides insights into normal physiologic processes, assists in elucidating the impact of factors in isolation and in combination with each other and allows dissection of disease processes such as neoplasia.

Preferred embodiments of the present invention are directed to assays for quantitating the effects of chemotactic and chemokinetic agents as well as inhibitors of cell migration on cells (e.g., cancer cells). The present invention is not limited however to providing assays for quantitating the effects of agents suspected of being involved in cancer formation and metastasis on cellular functions and motility.

Many motility factors for cancer cells and non-malignant cells were described first as being growth factors. A motility factor converts a static, adherent cell to a motile status, a transition that is characterized by the appearance of membrane ruffling, lamellae, filopodia and pseudopodia. Several motility factors have been described for cancer cells including: (1) autocrine motility factor (AMF) which stimulates chemokinesis and chemotaxis of metastatic melanoma cells in an autocrine fashion; (2) scatter factor/hepatocyte growth factor (e.g., ligands for the c-met oncogene product, a tyrosine kinase receptor family member); (3) TGF-α and EGF; (4) insulin-like growth factors; and (5) constituents of the extracellular matrix such as fibronectin; 6) PDGF; 7) LPA; 8) amphiregulin; and 9) chemokines. These factors stimulate chemokinesis and chemotaxis. The present invention specifically contemplates assays for detecting and quantifying the effects of one or more of these motility factors on cancer cell (and non-cancer cell) motility.

While metastatic cancer cells are thought to rely upon the processes of cell adhesion, deformability, motility, and receptor recognition for creating metastases, none of these processes are unique to metastatic cancer cells. These processes have been observed in numerous non-cancerous cell types and cellular processes (e.g., trophoblast implantation, mammary gland involution, embryonic morphogenesis, hematopoietic stem cells, and tissue remodeling).

Thus, certain embodiments of the present invention are directed to assays for quantifying the effects of potential cytoactive agents (e.g., mitogenic, growth inhibiting, chemotactic, and chemokinetic agents, inhibitors of cell migration, as well as agents that promote or inhibit cell adhesion, death, or differentiation) on cell types involved in fertility and conception, stem cell differentiation and proliferation, gene therapy and cell targeting, immunology, and diseases characterized by abnormal cell motility or migration. Certain other embodiments provide assays for quantitating the effects of cytoactive agents on bacteria, archaea, and eukarya. In certain embodiments the cytoactive agent being assayed is an attractant (e.g., positive chemotactic agent) of one or more cell types. In certain other embodiments the agent is a stimulant to cell migration but is non-directional in its effects (e.g., a chemokinetic agent). In certain other embodiments the cytoactive agent is an inhibitor or repellent of one or more cell types. In some embodiments, and in particular those embodiments directed to assays employing bacteria and archaea cells, potential tactic agents include, but are not limited to, phototaxis, aerotaxis, or osmotaxis agents, and the like.

The devices and methods of the present invention are useful with a variety of detection methodologies, including but not limited to liquid crystals, fluorimetry, densitometry, colorimetry, and radiometry.

The assays, systems, kits and methods of the present invention find use in discerning subtle changes in the motility of a cell (or particular type of cell). In some embodiments, cell motility is assayed upon contact with a suspected cytoactive agent. In some preferred embodiments, the present invention finds use in the detection and/or analysis of cells, including, but not limited to include, Chinese hamster ovary cells (CHO-K1, ATCC CC1-61); bovine mammary epithelial cells (ATCC CRL 10274; bovine mammary epithelial cells); monkey kidney CV1 line transformed by SV40 (COS-7, ATCC CRL 1651); human embryonic kidney line (293 or 293 cells subcloned for growth in suspension culture; see, e.g., Graham et al., J. Gen Virol., 36:59 [1977]); baby hamster kidney cells (BHK, ATCC CCL 10); mouse sertoli cells (TM4, Mather, Biol. Reprod. 23:243-251 [1980]); monkey kidney cells (CV 1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 [1982]); MRC 5 cells; FS4 cells; rat fibroblasts (208F cells); MDBK cells (bovine kidney cells); human hepatoma line (Hep G2), and, for example, the following cancerous cells or cells isolated from the following carcinomas: fibrosarcoma, myxosarcoma, liposarcoma, chondrosarcoma, osteogenic sarcoma, chordoma, angiosarcoma, endotheliosarcoma, lymphangiosarcoma, Ewing's tumor, lymphangioendotheliosarcoma, synovioma, mesothelioma, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilns' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease.

Furthermore, the assays of the present invention are readily adaptable to multi-array formats that permit simultaneous quantitation of the effects of one or more cytoactive agents upon one or more types of target cells and appropriate controls. Adaptability to multi-array formats also makes the assays of the present invention useful in high-throughput screening applications such as drug discovery.

In some particularly preferred embodiments, a biological moiety is covalently or noncovalently associated with the surface of the assay substrate so the response of a desired cell type to the biological moiety can be assayed. Suitable biological moieties include, but are not limited to, sugars, proteins (e.g., extracellular matrix proteins such as collagen, laminins, fibronectin, vitronectin, osteopontin, thromospondin, Intercellular adhesion molecule-1 (ICAM-1), ICAM-2, proteoglycans such as chondroitin sulfate, von Willebrand factor, entactin, fibrinogen, tenascin, Mucosal adressin cell adhesion molecule (MAdCAM-1), C3b, and MDC (metalloprotease/disintegrin/cysteine-rich) proteins), nucleic acids, specific receptors and cell receptor recognition sequences (e.g., cadherein, immunoglobulin superfamily, selectin, mucin, syndecan and integrin binding sequences, which, for itegrins are exemplified by but not limited to, RGD, EILDV, LDV, LDVP, IDAP, PHSRN, SLDVP, GRGDAC, and IDSP). In some embodiments, these biological moieties are associated with a substrate or surface that is ordered. In other embodiments, a surface or substrate with which biological moieties are associated is ordered by a method such as rubbing. It is contemplated that using rubbed protein/peptide substrate surfaces in the cell adhesion, migration, contraction and proliferation embodiments of the present invention allows researchers to investigate the impact of these constituents and to optimize assay conditions. For example, it is contemplated that the use of rubbed protein substrates will promote the adhesion of seeded cells and also promote cell function (e.g., such as adhesion, contraction, proliferation and migration). However, in some embodiments, it may be desirable to study cell function independent of the interaction of the rubbed protein substrates, thus, some embodiments employ polymeric substrates. Still other embodiments of the present invention provide substrates that combine attached protein/peptide moieties with non-biological forms of substrate functionalization and fabrication such as oblique deposition of gold and micromolded surfaces.

Some embodiments of the cell adhesion and proliferation assays of the present invention provide a plurality of distinct assay regions that allow for replicates of experimental conditions and controls to be run simultaneously. In still other preferred embodiments, the assay devices of the present invention are designed to have a footprint that is compatible with standard commercial plate readers (e.g., 24, 96, 384, 1536 etc., well plates). In still some other embodiments, simple nanostructured inserts are provided for use with commercial plates and plate readers.

Certain embodiments of the present invention provide assays for qualitatively and/or quantitatively determining the migration (e.g., random movement as well as attraction or repulsion) of cells on a substrate under control conditions and in response to one or more compounds of interest. In particular, the present invention contemplates, as described more fully below, a variety of assay formats optimized for distinguishing the positive, neutral or negative chemotactic and chemokinetic effects of one or more test compounds on cells of interest.

In some embodiments, the present invention provides cell invasion assays. It is contemplated that these assays are useful as an indication of neoplastic transformation and relative aggressiveness (invasiveness) of a tumor type. These in vitro assays are used to establish the effectiveness of therapeutic agents in preventing/minimizing invasion.

In some preferred embodiments, the extent of invasion of the ECM by placement of the liquid crystals on the ECM is read out. The present invention is not limited to any particular mechanism of action. Indeed, an understanding of the mechanism of action is not necessary to practice the present invention. Nevertheless, the process of invasion of the cells into the ECM leads to a change in the structure of the ECM that is reflected in the orientations of liquid crystals placed on to the surface. In a still further preferred embodiment of the invention, the ECM is prepared with a slightly anisotropic structure such that it uniformly orients the LC in the absence of invasion of the ECM by cells. Changes to the structure of the ECM caused by the invaded cells, lead to a disruption of the uniform orientation of the LC. In other embodiments of the invention, the process of invasion of the cells into the ECM leads to the introduction of anisotropic structure that is reflected in an increase in the order of LC placed onto the surface.

It is contemplated that this embodiment may also be employed in studies of cell biomechanics where subtle changes in surface mechanics caused by processes exemplified by, but not limited to, cell adhesion, migration and contraction are reported by alterations in LC orientation that are observable by viewing with polarized light and the appropriate use of filters and by the use of certain wavelengths of light.

In another embodiment of the invention, hybrid three-dimensional matrices composed of ordered LC and of extracellular matrix (ECM) constituents are provided that would support cell function upon or within the matrix. In preferred embodiments, the hybrid matrix is formed by gelling an admixture of constituents (singly or together) exemplified by, but not limited to, mesogens, sugars, proteins (e.g., extracellular matrix proteins such as collagen, laminin, fibronectin, vitronectin, osteopontin, thromospondin, Intercellular adhesion molecule-1 (ICAM-1), ICAM-2, proteoglycans such as chondroitin sulfate, von Willebrand factor, entactin, fibrinogen, tenascin, Mucosal adressin cell adhesion molecule (MAdCAM-1), C3b, and MDC (metalloprotease/disintegrin/cysteine-rich) proteins), nucleic acids, specific receptors or cell receptor recognition sequences (e.g., cadherein, immunoglobulin superfamily, selectin, mucin and integrin binding sequences such as RGD, EILDV, LDV, LDVP, IDAP, PHSRN, SLDVP, GRGDAC, and IDSP). In preferred embodiments, the gel process is conducted while applying an orienting electric field. This results in a matrix with aligned mesogens that are stable after gelling. It is contemplated that this gelling procedure also orients the other matrix constituents (depending on their relative charge and asymmetry of charge distribution).) The oriented hybrid composite can be prepared by using electric fields, magnetic fields, or by mechanical shearing of the composite. In some embodiments, commercially available basement membrane-like complexes (e.g., Matrigel™, which is harvested from a transformed cell line (EHS)) are used as the ECM constituent admixed with the liquid crystalline species. The liquid crystals can be thermotropic or lyotropic liquid crystals. If lyotropic liquid crystals, then preferred mesogens include non-membrane disrupting surfactants, and discotic mesogens that are not membrane disrupting.

In some embodiments, the assay devices and systems of the present invention find use in the assay of compounds that are suspected of influencing cell migration, cell motility, cell invasion, chemotaxis, and the like. In some embodiments, the test compounds are contacted with the assay cells on the assay substrate, such as by adding the test compounds to a well in a multiwell plate. In other embodiments, test compound regions are provided on the assay substrate in the form a porous or nonporous material that releases a given test compound into the assay device.

Suitable test compounds but are not limited to, small organic compounds, amino acids, vitamins and peptides and polypeptides, including, but not limited to, magainin (e.g., magainin I, magainin II, xenopsin, xenopsin precursor fragment, caerulein precursor fragment), magainin I and II analogs (PGLa, magainin A, magainin G, pexiganin, Z-12, pexigainin acetate, D35, MSI-78A, MG0 [K10E, K11E, F12W-magainin 2], MG2+[K10E, F12W-magainin-2], MG4+[F12W-magainin 2], MG6+[ f12W, E19Q-magainin 2 amide], MSI-238, reversed magainin II analogs [e.g., 53D, 87-ISM, and A87-ISM], Ala-magainin II amide, magainin II amide), cecropin P1, cecropin A, cecropin B, indolicidin, nisin, ranalexin, lactoferricin B, poly-L-lysine, cecropin A (1-8)-magainin II (1-12), cecropin A (1-8)-melittin (1-12), CA(1-13)-MA(1-13), CA(1-13)-ME(1-13), gramicidin, gramicidin A, gramicidin D, gramicidin S, alamethicin, protegrin, histatin, dermaseptin, lentivirus amphipathic peptide or analog, parasin I, lycotoxin I or II, globomycin, gramicidin S, surfactin, ralinomycin, valinomycin, polymyxin B, PM2 [(+/−) 1-(4-aminobutyl)-6-benzylindane], PM2c[(+/−)-6-benzyl-1-(3-carboxypropyl)indane], PM3 [(+/−)1-benzyl-6-(4-aminobutyl)indane], tachyplesin, buforin I or II, misgurin, melittin, PR-39, PR-26, 9-phenylnonylamine, $(KLAKKLA)_n$, $(KLAKLAK)_n$, where n=1, 2, or 3, $(KALKALK)_3$, $KLGKKLG)_n$, and $KAAKKAA)_n$, wherein N=1, 2, or 3, paradaxin, Bac 5, Bac 7, ceratoxin, mdelin 1 and 5, bombin-like peptides, PGQ, cathelicidin, HD-5, Oabac5alpha, ChBac5, SMAP-29, Bac7.5, lactoferrin, granulysini, thionin, hevein and knottin-like peptides, MPG1, 1bAMP, lipid transfer proteins, Insulin, Insulin like Growth Factors such as IGF-I, IGF-II, and IGF-BP; Epidermal Growth Factors such as α-EGF and β-EGF; EGF-like molecules such as Keratinocyte-derived growth factor (which is identical to KAF, KDGF, and amphiregulin) and vaccinia virus growth factor (VVGF); Fibroblast Growth Factors such as FGF-1 (Basic FGF Protein), FGF-2 (Acidic FGF Protein), FGF-3 (Int-2), FGF-4 (Hst-1), FGF-5, FGF-6, and FGF-7 (identical to KGF); FGF-Related Growth Factors such as Endothelial Cell Growth Factors (e.g., ECGF-α and ECGF-β); FGF— and ECGF—Related Growth Factors such as Endothelial cell stimulating angiogenesis factor and Tumor angiogenesis factor, Retina-Derived Growth Factor (RDGF), Vascular endothelium growth factor (VEGF), Brain-Derived Growth Factor (BDGF A- and -B), Astroglial Growth Factors (AGF 1 and 2), Omentum-derived factor (ODF), Fibroblast-Stimulating factor (FSF), and Embryonal Carcinoma-Derived Growth Factor; Neurotrophic Growth Factors such as α-NGF, β-NGF, γ-NGF, Brain-Derived Neurotrophic Factor (BDNF), Neurotrophin-3, Neurotrophin-4, and Ciliary Nuerotrophic Factor (CNTF); Glial Growth Factors such as GGF-I, GGF-II, GGF-III, Glia Maturation Factor (GMF), and Glial-Derived Nuerotrophic Factor (GDNF); Organ-Specific Growth Factors such as Liver Growth Factors (e.g., Hepatopoietin A, Hepatopoietin B, and Hepatocyte Growth Factors (HCGF or HGF), Prostate Growth Factors (e.g., Prostate-Derived Growth Factors [PGF] and Bone Marrow-Derived Prostate Growth Factor), Mammary Growth Factors (e.g., Mammary-Derived Growth Factor 1 [MDGF-1] and Mammary Tumor-Derived Factor [MTGF]), and Heart Growth Factors (e.g., Nonmyocyte-Derived Growth Factor [NMDGF]); Cell-Specific Growth Factors such as Melanocyte Growth Factors (e.g., Melanocyte-Stimulating Hormone [α-, β-, and γ-MSH] and Melanoma Growth-Stimulating Activity [MGSA]), Angiogenic Factors (e.g., Angiogenin, Angiotropin, Platelet-Derived ECGF, VEGF, and Pleiotrophin), Transforming Growth Factors (e.g., TGF-α, TGF-β, and TGF-like Growth Factors such as TGF-$\beta_2$, TGF-$\beta_3$, TGF-e, GDF-1, CDGF and Tumor-Derived TGF-β-like Factors), ND-TGF, and Human epithelial transforming factor [h-TGFe]); Regulatory Peptides with Growth Factor-like Properties such as Bombesin and Bombesin-like peptides (e.g., Ranatensin, and Litorin], Angiotensin, Endothelin, Atrial Natriuretic Factor, Vasoactive Intestinal Peptide, and Bradykinin; Cytokines such as the interleukins IL-1 (e.g., Osteoclast-activating factor [OAF], Lymphocyte-activating factor [LAF], Hepatocyte-stimulating factor [HSF], Fibroblast-activating factor [FAF], B-cell-activating factor [BAF], Tumor inhibitory factor 2 [TIF-2], Keratinocyte-derived T-cell growth factor [KD-TCGF]), IL-2 (T-cell growth factor [TCGF], T-cell mitogenic factor [TCMF]), IL-3 (e.g., Hematopoietin, Multipotential colony-stimulating factor [multi-CSF], Multilineage colony-stimulating activity [multi-CSA], Mast cell growth factor [MCGF], Erythroid burst-promoting activity [BPA-E], IL-4 (e.g., B-cell growth factor I [BCGF-1], B-cell stimulatory factor 1 [BSF-1]), IL-5 (e.g., B-cell growth factor II [BCGF-II], Eosinophil colony-stimulating factor [Eo-CSF], Immunoglobulin A-enhancing factor [IgA-EF], T-cell replacing factor [TCRF]), IL-6 (B-cell stimulatory factor 2 [BSF-2], B-cell hybridoma growth factor [BCHGF], Interferon $\beta_2$ [IFN-B], T-cell activating factor [TAF], IL-7 (e.g. Lymphopoietin 1 [LP-1], Pre-B-cell growth factor [pre-BCGF]), IL-8 (Monocyte-derived neutrophil chemotactic factor [MDNCF], Granulocyte chemotatic factor [GCF], Neutrophil-activating peptide 1 [NAP-1], Leukocyte adhesion inhibitor [LAI], T-lymphocyte chemotactic factor [TLCF]), IL-9 (e.g., T-cell growth factor III [TCGF-III], Factor P40, MegaKaryoblast growth factor (MKBGF), Mast cell growth enhancing activity [MEA or MCGEA]), IL-10 (e.g., Cytokine synthesis inhibitory factor [CSIF]), IL-11 (e.g., Stromal cell-derived cytokine [SCDC]), IL-12 (e.g., Natural killer cell stimulating factor [NKCSF or NKSF], Cytotoxic lymphocyte maturation factor [CLMF]), TNF-α (Cachectin), TNF-β (Lymphotoxin), LIF (Differentiation-inducing factor [DIF], Differentiation-inducing activity [DIA], D factor, Human interleukin for DA cells [HILDA], Hepatocyte stimulating factor III [HSF-III], Cholinergic neuronal differentiation factor [CNDF], CSF-1 (Macrophage colony-stimulating factor [M-CSF]), CSF-2 (Granulocyte-macrophage colony-stimulating factor [GM-CSF]), CSF-3 (Granulocyte colony-stimulating factor [G-CSF]), and erythropoietin; Platelet-derived growth factors (e.g., PDGF-A, PDGF-B, PDGF-AB, p28-sis, and p26-cis), and Bone Morphogenetic protein (BMP), neuropeptides (e.g., Substance P, calcitonin gene-regulated peptide, and neuropeptide Y), and neurotransmitters (e.g., norepinephrine and acetylcholine).

Accordingly, in some embodiments, the present invention provides an assay apparatus comprising a surface having at least one discrete assay region thereon and wherein the assay region is associated with at least one test compound formulated for controlled release. In some embodiments, the test compound formulated for controlled release is provided in a matrix. In some embodiments, the matrix is a polymer. Various polymers that find use for controlled release applications, include, but are not limited to chitosan, chitosan-alginate, poly(N-isopropylacrylamide) hydrogels, lipid microspheres, copolymers of polylactic and polyglycolic acid, dextran hydrogels, and poly(ethylene glycol) hydrogels. (See, e.g., Zambito et al., Acta Technol. Et Legis Medicamenti 14(1): 1-11 (2003); Bhopaktar et al., Advances Chitin Sci. 5:166-170 (2002); Zhuo et al., J. Polymer Sci. 41(1):152-159 (2002); Del Curto et al., Proceedings of the 28th Symposium on Controlled Release of Bioactive Materials, San Diego, Calif., 2:976-977 (2001); Hu et al., J. Drug Targeting 9(6):431-438 (2001); Lambert et al., J. Controlled Release 33(1):189-195 (1995); Hennink et al., J. Controlled Release 48(2, 3):107-114 (1997); and Zhoa et al., J. Pharm. Sci. 87(11):1450-1458 (1998). In some embodiments, the matrix further comprises an extracellular matrix component (e.g., collagen, vitronectin, fibronectin or laminin). A variety of test compounds may be provided in the matrix, including, but not limited to, polypeptides, carbohydrates, amino acids, and small organic compounds. These assay devices may be used with any of the read out and labeling methods described herein, including LC based assays, calorimetric assays, fluorimetric assays, optical density assays, and light scattering assays. In other embodiments, the assay devices are configured with a plurality of assay regions corresponding spatially to the wells of 6, 12, 24, 36, 96, 384 or 1536 well plates. The matrix containing the test compound may be provided in a variety of orientations, for example on the bottom of a well or other assay region, on the side of a well, as a strip in the bottom or side of well or other assay region, or as a bead on an interior surface of a well or on an assay region.

In still further embodiments, the present invention provides kits comprising an assay apparatus comprising a surface having thereon at least one discrete assay region and unpolymerized matrix material. In some embodiments, the discrete assay region further comprises a cell seeding region. In some embodiments, the kits provide instructions for polymerizing the matrix material in the presence of at least one test compound, applying the matrix to an apparatus, and culturing cells in the apparatus. It is contemplated that foregoing apparatuses find use in assaying the response of cells to a stimulus from a test compound. The apparatuses may also be utilized in high-throughput settings to measure the effect of a panel or library of compounds on cells.

In still further embodiments, test compound regions are provided by the differential movement of materials (e.g., test compounds) by the manipulation of electrical fields, thermal gradients, and capillary action on the substrate surface. In other preferred embodiments of the invention, chemotactic or chemokinetic agents are immobilized on the surfaces. These agents can be presented in uniform concentration on a surface, they can be patterned on a surface or they can be present in a gradient in concentration across a surface. The agents immobilized on the surface may be released from the surface to make them available to the cells by using changes in the microenvironment of the surfaces caused by the cells to trigger the release of the agents, or externally controlled variables (such as illumination or applied electrical potentials) can be used to regulate the release of the agents from the surface. In other preferred embodiments of the invention, the agents are not released from the surface but interact with constituents of the membrane of the cell and thereby influence cell behavior.

In some further preferred embodiments, the assay regions of the devices are associated with a biological moiety. In some embodiments, a disordered (e.g., randomly ordered) substrate or assay region on a substrate appropriate for assays disclosed herein is created by attaching (e.g., covalently or noncovalently) one or more biologic moieties, (e.g., sugars, proteins (e.g., extracellular matrix proteins such as collagen, laminin, fibronectin, vitronectin, osteopontin, thromospondin, Intercellular adhesion molecule-1 (ICAM-1), ICAM-2, proteoglycans such as chondroitin sulfate, von Willebrand factor, entactin, fibrinogen, tenascin, Mucosal adressin cell adhesion molecule (MAdCAM-1), C3b, and MDC (metalloprotease/disintegrin/cysteine-rich) proteins), nucleic acids, specific receptors or cell receptor recognition sequences (e.g., cadherin, immunoglobulin superfamily, selectin, mucin and integrin binding sequences such as RGD, EILDV, LDV, LDVP, IDAP, PHSRN, SLDVP, GRGDAC, and IDSP)) onto a suitable substrate surface. In another embodiment, an ordered substrate or assay region on a substrate is created by covalently or noncovalently binding one or more or the previously described biological moieties to a polymeric surface and subsequently rubbing the surface to create order. The present invention is not intended to be limited by the order of steps taken in creating a suitable substrate surface. For example, in some embodiments, the substrate is ordered prior to the attachment of biological moieties. In other embodiments, the substrate is ordered after addition of biological moieties. Indeed, a number of processing events and steps are adaptable to producing suitable substrate compositions for use in the assays disclosed herein given the specific guidance provided and the skill of those in the art.

In other embodiments, an ordered substrate is created by contacting a suitable surface with a plurality of evenly distributed particles (e.g., magnetic nanoparticles) that when aligned orient a mesogenic layer. As described in detail above, the particles may be applied to the surface (positive nanostamp) or removed from the surface (negative nanostamp) with nanostamping devices (ref. FIGS. 1A and 1B). In particularly preferred embodiments, the particles are magnetic nanoparticles that are aligned using a magnetic field. In another preferred embodiment, the metallic nanorods are small enough to be readily displaced by migrating cells.

In some embodiments of the present invention, the extent of overall cell movement in the assay device is determined by analyzing the number or proportion of the cells in the cell exclusion zone of the assay substrate. Preferred methods for analyzing the number of cells present include detection of the cells via fluorescent labeling and visualization with liquid crystals. The number of cells within the cell exclusion zone generally corresponds to light emitted from the fluorescently labeled cells. In some embodiments, the number of cells in the cell exclusion zone is analyzed in the presence and absence of particular compound, or other suitable controls are performed in parallel.

In some embodiments, the assay devices are used to investigate cell invasion, processes related to cell invasion, and compounds that inhibit or stimulate cell invasion. In some embodiments, a protein or matrix is coated onto the well bottoms and then as described in detail above, an analytic cell free zone is established. Cells are seeded into the permissive area and a matrix is installed that covers the cells and the analytic zone. Following incubation to allow cells to invade, the assay plate is read to determine the movement of cells into the analytic zone. In other embodiments, the cells are delivered to the wells while suspended in a matrix and seeded in a 3-dimensional manner in the permissive area. A matrix is added to the wells to cover the analytic zone and the plate is incubated to allow cells to invade. In still other embodiments, a matrix is coated in the wells, then cells suspended in matrix are added to the well, and the analytic zone is coated with a layer of the matrix.

IV. Kits

It will be appreciated that the various components of the cell assay systems described above, including, but not limited to the cell assay substrates, polymeric inserts, masks, fluorescent labels, control samples, can be provided as part of systems and kits for assaying cell migration. In preferred embodiments, these systems and kits include multiwell plates and the inserts are configured to be inserted into the multiwell plates. In further embodiments, the kits of the present invention include instructions for conducting cell migration assays. In some embodiments, the instructions further comprise the statement of intended use required by the U.S. Food and Drug Administration (FDA) in labeling in vitro diagnostic products. The FDA classifies in vitro diagnostics as medical devices and requires that they be approved through the 510(k) procedure. Information required in an application under 510(k) includes: 1) The in vitro diagnostic product name, including the trade or proprietary name, the common or usual name, and the classification name of the device; 2) The intended use of the product; 3) The establishment registration number, if applicable, of the owner or operator submitting the 510(k) submission; the class in which the in vitro diagnostic product was placed under section 513 of the FD&C Act, if known, its appropriate panel, or, if the owner or operator determines that the device has not been classified under such section, a statement of that determination and the basis for the determination that the in vitro diagnostic product is not so classified; 4) Proposed labels, labeling and advertisements sufficient to describe the in vitro diagnostic product, its intended use, and directions for use. Where applicable, photographs or engineering drawings should be supplied; 5) A statement indicating that the device is similar to and/or different from other in vitro diagnostic products of comparable type in commercial distribution in the U.S., accompanied by data to support the statement; 6) A 510(k) summary of the safety and effectiveness data upon which the substantial equivalence determination is based; or a statement that the 510(k) safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; 8) Any additional information regarding the in vitro diagnostic product requested that is necessary for the FDA to make a substantial equivalency determination. Additional information is available at the Internet web page of the U.S. FDA. It will be further recognized that the cell seeding inserts can be used in methods, systems, and kits which utilize a variety of detection methods, including but not limited to calorimetric, fluorimetric, light scattering, liquid crystal, densitometric, and microscopic assays.

EXPERIMENTAL

Example 1

Demonstration of Mask Functionality

A 100 ul portion of 3T3 fibroblasts (at 25,000 cells per well and treated with mitomycin C to inhibit proliferation) were seeded into wells of a Greiner 96-well flat bottom plate that contained cell seeding inserts. The fibroblasts were allowed to adhere for four hours at 37° C., 5% CO2. The inserts were then removed from the test wells and the wells were washed with PBS to remove non-adhered cells. A 100 ul volume of cell culture media (MEM containing 10% FBS) was then introduced into each well. In negative control wells, the seeding inserts remained in place for the duration of the incubations. The seeded plate was incubated overnight (~21 hours) to permit migration of the cells in the test wells. Following incubation, the inserts were removed from the control wells. All wells were washed with PBS and the cells were stained with a fluorescent Calcein AM dye using standard methods per manufacturer instructions. The well contents were observed by using an Zeiss Axiovert microscope (2.5× objective, FITC filter) and digital images were captured both in the absence and presence of the mask.

The amount of fluorescent signal was quantified by use of a plate reader. Briefly, the plate was inserted into the Bio-Tek Synergy plate reader and fluorescence signal was measured by using parameters that included 528/533 nm wavelength, a gain sensitivity of 55, and a bottom probe read. The relative fluorescence units (RFUs) were captured with the mask in place for both the control and test wells (N=8 replicates per condition). The RFU data was subjected to a 5PLE calculation that converts signal detected into numbers of cells present. The results of this study indicated that the fluorescence signal in the analytic zone of the test wells represented 240+/−37 cells while that signal in the control wells represented 29+/−8 cells (data not shown).

Example 2

Influence of Mask Aperture Size

An analysis of migration assay performance was performed using a set of machined masks, each having 96 apertures of a defined diameter. The aperture diameters tested ranged from 1.8 to 2.3 mm in 0.1 mm increments.

Cells were seeded into four assay plates containing the silicone inserts and cultured overnight to allow the cells to attach. At this point, the inserts were removed from two of the four plates. The inserts were left in place in the other two plates to serve as controls. Two migration intervals (6 and 22 hours) were evaluated. Following each time interval one test and one control plate was stained with Calcein AM. After 22 hrs over 90% of the analytical area in the wells of the test plate contained cells.

To determine the extent of cell migration into the exclusion zone, each of the six masks with apertures ranging from 1.8-2.3 mm were fit to the bottom of the stained plates. The prototype masks do not have a complete set of registration pins, thus each mask was taped to the bottom of the plate. To compensate for the likely registration errors due to the application method, three separate fittings of a given mask were read on the fluorescent microplate reader. The data from the three fittings were averaged for statistical analysis.

The bowing of the mask towards the outer edges of the plate causes the effective aperture opening to depart from a circle to an ovoid, reducing the detection area. As this effect was most pronounced at the edges of the plate, data from columns 1, 2, 11, and 12 was found to have the greatest interference and was not used for the analysis. Data is graphically presented below in raw form, as Effect Size, and as the Signal to Noise ratio. The delta, calculated by subtraction of the average migration signal from the control signal is also presented. See FIGS. 14A-C, 15A-C and 16 for the data.

The dynamic range of the assay was reduced by the smaller (1.8-2.0 mm) apertures. The 1.8 or 1.9 mm mask decreased the dynamic range especially at later time points in the migration assay (22 hours). The 2.3 mm mask significantly increased background at both 6 hr and 22 hr migration time points. The 2.0 and 2.1 mm masks resulted in the greatest Effect Size. The data treatment where the difference in fluorescence levels between test and control conditions is calculated suggests the larger apertures result in higher signal intensity. The average cell exclusion zone diameter for the current tip design (mold not plated) is 1990-2000 microns. The cell exclusion zone referred to here is the measured diameter of unstained area in a control plate, not the insert tip diameter. Under the conditions tested, the 2.1 mm mask appears to balance background with signal and seems to be ideal.

We have evaluated a range of mask aperture diameters that could be used to detect cells in early and late stages of migration. In this study, the smaller mask diameters reduced dynamic range and prevented early detection of cell migration, while mask apertures slightly larger than the cell exclusion zone provided the best Effect Size. As the dimensional and registration tolerances of the final molded mask are unknown at this time, a mask diameter approximately 100 microns larger than the expected cell exclusion zone should balance the various design and performance considerations.

Example 3

Photoimmobilized Hyaluronic Acid Transiently Disrupts Cell Adherence to Tissue Culture Plate Surfaces This example describes the ability to block adhesion of HT-1080 cells to a surface coated with hyaluronic acid (HA). The HA was functionalized with a photoactive linker and immobilized to the bottom of a well in a tissue culture plate. The material was prepared by reacting the carboxyl group of HA disaccharides with the amine group of a heterobifunctional crosslinker (4-[p-azidosalicylamido]butylamine, ASBA) via carbodiimide chemistry. The other end of the ASBA crosslinker contains a photoactive group, so this reaction renders the HA photoactive. Carboxylate modifications of the HA do not affect its degradability by hyaluronidase (HA-ase). Briefly, the HA was dissolved in MES buffer and reacted with EDC and Sulfo-NHS for 15 min at room temperature. The pH of the buffer was adjusted to ca. 7.0 with concentrated PBS and ASBA was added to the solution and allowed to react for 2 h at room temperature in a light-proof vial. The reaction was quenched using 50 mM Tris. Unreacted components and reaction by-products were removed via dialysis against diH2O using a 3,000 MW exclusion. The reaction product was protected from exposure to light during lyophilization. Three species of photoactive HA were prepared that varied according to the molecular weight of the HA chains: low, medium and high MW chains.

The lyophilized, photoactive HA was reconstituted in PBS and adjusted to a working concentration of 0.2 mg/ml. A 40 ul volume of photoactive HA was pipetted into wells of a 96-well plate and the solution allowed to dry overnight at 40° C. with gentle shaking. The plates were exposed to a 365 nm, 90 mW/cm2 UV light source (Omnicure 2000, Exfo, Inc.) for 2 min to create the chemically engineered exclusion zone. Following UV exposure, the wells were washed 3× with diH2O and then refilled with diH2O for a 24 h room temperature rinse on a shaking platform (30 rpm). The plate, now with HA immobilized on the well bottoms, was sterilized by exposure to 254 nm UV light for one hour.

Wells containing immobilized HA were seeded with 40,000 HT-1080 cells overnight. Observations were made and images captured as to the nature of the adherence of the cells to this material before and after a 30 minute treatment with hyaluronidase (HA-ase; 50 microliters of a 1000 U/ml solution).

Crosslinking of HA to the wells had a progressive effect on the morphology of attached cells that was dependent on the molecular weight of the HA chains photoimmobilized to the well surface. The low molecular weight HA material had little, if any, discernable morphological effect on cells as compared to cells attached tissue culture treated wells (Condition 1). Cells began to exhibit some balling up on mid-range molecular weight HA as depicted in Condition 2. Cells seeded onto high molecular weight HA material exhibited frank changes in morphology, appearing as gross clusters on the surface with large areas where cells did not attach (Condition 3).

Subsequent hyaluronidase treatment of cells grown on Conditions 2 and 3 caused a marked reversal of the clustering morphology, with cells in Condition 2 appearing morphologically identical to cells treated with HA-ase in tissue culture treated wells and the cells in Condition 3 appearing with many fewer clusters. Enzymatic treatment with HA-ase allows these clusters to “relax” or disperse once again on the well surface. Hyaluronidase treatment did not have a significant effect on cells attached to control wells not phototreated with HA; the cells were still firmly attached to the plate bottoms and did not appear morphologically altered in any gross fashion.

HA prevents uniform cell attachment to the surface of a tissue culture well plate. The ability of HA to function in this capacity is proportional to the molecular weight/overall size of the HA chains. The ability of HA to cause exclusion/clustering of cells is reversible upon treatment with hyaluronidase enzyme. HA-ase treatment does not cause any gross morphological changes or have any toxic effects to cells attached to non-Ha treated tissue culture surfaces.

Example 4

Use of Dissolving Polymer to Create Exclusion Zone

Figure 17:
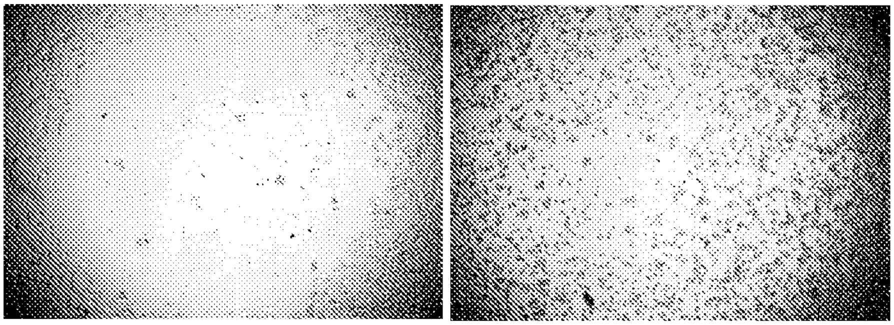
FIG. 17 shows the use of a dissolving polymer to create an exclusion zone.

Polyvinyl alcohol (PVA), average molecular weight 22,000, was dispensed in an equal weight of hot water and allowed to completely dissolve. A micropipette was used to dispense 2.5 microliters of PVA into the center of the wells of a 96-well plate having an optically clear, tissue culture treated bottom. The plate was placed in a 50° C. oven to evaporate the water from the PVA spot, forming a round, transparent film in the center of the well. To start the assay, 35000 HT1080 cells suspended in 100 μl complete tissue culture medium were added to each well and cultured at 37° C., 5% $CO_2$ for 24 hours. Each well was then washed once with PBS before 100 μl fresh complete medium was added. The washing effectively removed the PVA from the center of the well. Results are shown in FIG. 17. FIG. 17*a* shows a representative well following the PBS wash. As shown, cells have attached in the perimeter of the well but were not permitted to attach in the center of the well previously occupied by the PVA. The plates were then returned to 37° C., 5% $CO_2$ for 48 hours and photographed again (FIG. 17B). No exclusion was observed for control wells run in parallel, including wells without PVA, or wells spotted with solutions of 50% polyethylene glycol or 25% polyvinylpyrrolidone. These findings indicate that while PVA can be used to restrict cell attachment.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in chemical engineering, cell biology, or molecular biology or related fields are intended to be within the scope of the following claims.

We claim:

1. A cell assay device comprising:

a multiwell plate comprising a plurality of wells having one or more cell assay zones on the bottom surface of said wells in said multiwell plate, said assay zones comprising one or more spatially distinct cell seeding zones comprising a surface to which cells can adhere positioned adjacent to one or more spatially distinct cell exclusion zones comprising a blocking material deposited on said bottom surface of said wells to block adherence of cells to the surface of said cell exclusion zone, wherein said blocking material is selected from the group consisting of poly n-butyl hemiester of [poly(maleic anhydride-alt-2-methoxyethyl-vinyl ether), poly N-isopropylacrylamide, poly(lactic acid), poly[(lactic acid-co-(glycolic acid)], poly(ethylene oxide), poly(propylene oxide), N-isopropylacrylamide copolymers, cellulose acetate butyrate polymers, perfluorocarbon terminated polymers, poly(N,N-diethylacrylamide), N-isopropylacrylamide, diethyleneglycol methacrylate (poly(NiPAAm-co-DEGMA) copolymers, alginate, starch glycogen, chitin, xanthan gum, dextran, gellan gum, glucomannan, hydroxypropyl cellulose, hydroxypropylmethyl cellulose, carboxymethyl cellulose, carageenan, inulin, agarose, polyvinyl alcohol, pullulan, and nucleic acids, wherein said blocking material dissolves upon exposure to an aqueous cell culture medium to expose a surface to which cells can adhere.

2. The cell assay device of claim 1, wherein said cell seeding zones are coated with a coating material comprising protein or polysaccharide.

3. The cell assay device of claim 1, wherein said blocking material is selected from the group consisting of poly(lactic acid), poly[(lactic acid-co-(glycolic acid)], cellulose acetate butyrate polymers, and polyvinyl alcohol.

4. The cell assay device of claim 1, further comprising a non-degradable layer adhered to said blocking material.

5. The cell assay device of claim 1, wherein said blocking material can be modified to allow cell adherence.

6. The cell assay device of claim 1, further comprising a mask configured to interface with said substrate.

7. The cell assay device of claim 6, said mask having a array of apertures therein so that when said mask is placed adjacent to said substrate said one or more cells assay zones is aligned with said array of apertures, wherein a portion of the cell exclusion zone is exposed by the aperture.

8. The cell assay device of claim 1, wherein said multiwell plate is selected from the group consisting of 6, 12, 24, 48, 96, 384 and 1536 well plates.

* * * * *